(12) United States Patent
Dahl et al.

(10) Patent No.: US 11,564,695 B2
(45) Date of Patent: *Jan. 31, 2023

(54) TOURNIQUET

(71) Applicant: ORTRUD MEDICAL AB, Stockholm (SE)

(72) Inventors: Caroline Dahl, Stockholm (SE); Patrik J. Nilsson, Stockholm (SE)

(73) Assignee: ORTRUD MEDICAL AB (*) Notice: Subject to any disclaimer, the term of this patent is extended or adjusted under 35 U.S.C. 154(b) by 483 days.

This patent is subject to a terminal disclaimer.

(21) Appl. No.: 16/630,548

(22) PCT Filed: Jul. 6, 2018

(86) PCT No.: PCT/SE2018/050744
§ 371 (c)(1),
(2) Date: Jan. 13, 2020

(87) PCT Pub. No.: WO2019/017827
PCT Pub. Date: Jan. 24, 2019

(65) Prior Publication Data
US 2021/0113213 A1    Apr. 22, 2021

(30) Foreign Application Priority Data
Jul. 17, 2017    (SE) .................................. 1700147-0

(51) Int. Cl.
A61B 17/00    (2006.01)
A61B 17/132    (2006.01)
(Continued)

(52) U.S. Cl.
CPC .......... A61B 17/1322 (2013.01); A61B 50/33 (2016.02); A61B 90/06 (2016.02); A61B 2090/064 (2016.02)

(58) Field of Classification Search
CPC .......... A61B 17/1322; A61B 2090/064; A61B 50/30; A61B 50/33; A61B 90/06; A61B 17/132; A61F 5/32
See application file for complete search history.

(56) References Cited

U.S. PATENT DOCUMENTS 3,613,679 A    10/1971    Bijou et al.
4,700,715 A    10/1987    Levine et al.
(Continued)

FOREIGN PATENT DOCUMENTS

CN    102939054    2/2013
CN    103354733    10/2013
(Continued)

OTHER PUBLICATIONS

Extended European Search Report dated May 14, 2020; European Patent Application No. 18834713.2.
(Continued)

Primary Examiner — Thien M Le
(74) Attorney, Agent, or Firm — McDonald Hopkins LLC

(57) ABSTRACT

The present disclosure relates to a tourniquet 1 comprising a tension sensor 8 and loop portion 4 ensuring that an intended pressure has been achieved on a body part on which the tourniquet is applied. The tension sensor comprises a plurality of cuts 20 arranged in a predetermined pattern. The present disclosure also relates to a dispenser comprising a plurality of such tourniquets, and a kit comprising a tourniquet.

29 Claims, 8 Drawing Sheets

(51) Int. Cl.
*A61B 50/33* (2016.01)
*A61B 90/00* (2016.01)

(56) References Cited

U.S. PATENT DOCUMENTS

| | | | |
|---|---|---|---|
| 5,219,356 A | 6/1993 | Harreld et al. | |
| 6,638,073 B1* | 10/2003 | Kazimirov | G09B 23/30 434/272 |
| 8,827,720 B1* | 9/2014 | Lazarus | G09B 23/32 434/262 |
| 2005/0038442 A1* | 2/2005 | Freeman | A61B 5/4528 606/86 R |
| 2006/0064082 A1* | 3/2006 | Bonutti | A61B 5/055 606/32 |
| 2008/0227073 A1* | 9/2008 | Bardsley | G09B 23/34 434/267 |
| 2008/0262535 A1 | 10/2008 | Gavriely et al. | |
| 2008/0264327 A1 | 10/2008 | Pett et al. | |
| 2009/0085444 A1* | 4/2009 | Alvarez Icaza Rivera | H02N 11/006 310/365 |
| 2009/0112145 A1* | 4/2009 | Lecomte | A61F 13/0273 602/76 |
| 2009/0168612 A1 | 7/2009 | Robin et al. | |
| 2010/0217202 A1 | 8/2010 | Clark | |
| 2012/0330192 A1* | 12/2012 | Casey | A61B 17/135 600/587 |
| 2013/0304113 A1 | 11/2013 | Eikman et al. | |
| 2014/0277101 A1 | 9/2014 | Smith et al. | |
| 2015/0119926 A1 | 4/2015 | Saatchi et al. | |
| 2016/0287262 A1 | 10/2016 | Kirchner et al. | |
| 2016/0317159 A1 | 11/2016 | Smith et al. | |
| 2017/0312165 A1* | 11/2017 | Johnson | A61B 5/021 |
| 2019/0247121 A1* | 8/2019 | Douglas | A61B 34/10 |

FOREIGN PATENT DOCUMENTS

| | | |
|---|---|---|
| CN | 203852391 | 10/2014 |
| DE | 102015103346 A1 | 9/2016 |
| GB | 2485572 | 5/2012 |
| GB | 2542412 A | 3/2017 |
| GB | 2543485 A | 4/2017 |
| JP | 2009-511870 | 4/2007 |
| JP | 2014-531959 | 12/2014 |
| JP | 2015-518927 | 7/2015 |
| JP | 2015-221212 | 12/2015 |
| WO | 200606664 | 1/2006 |
| WO | 2009046518 A1 | 4/2009 |
| WO | 2014113036 A1 | 7/2014 |
| WO | 2014114604 A1 | 7/2014 |

OTHER PUBLICATIONS

Japan Patent Office (JPO), Notification of Reasons for Rejection for Patent Application No. 2019-571341, dated Mar. 14, 2022, Second Patent Examination Department, Japan.

Intellectual Property of India, Examination Report for Application No. 202047001319, dated Mar. 3, 2022.

International Search Report and Written Opinion dated Sep. 21, 2018; International Patent Application No. PCT/SE2018/050744 filed Jul. 6, 2018. ISA/SE.

State Intellectual Property Office of People's Republic of China, Notification of First Office Action for Application No. 022062501414240, dated Jun. 29, 2022, China.

* cited by examiner

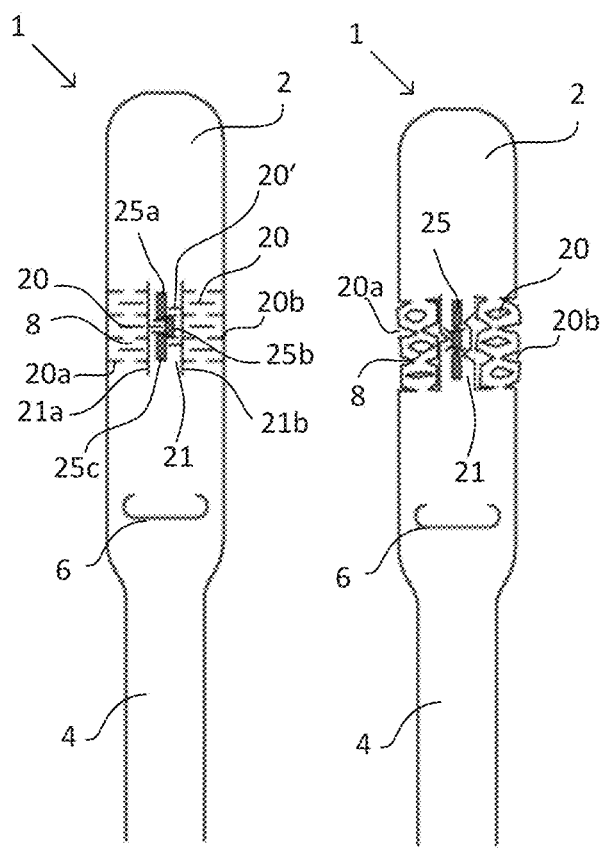
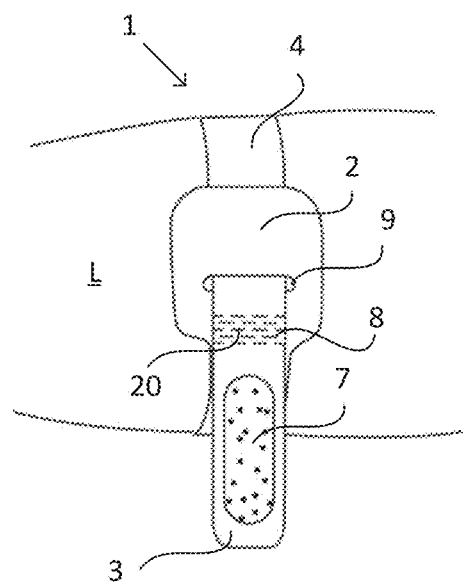
Fig. 4a    Fig. 4b    Fig. 5a
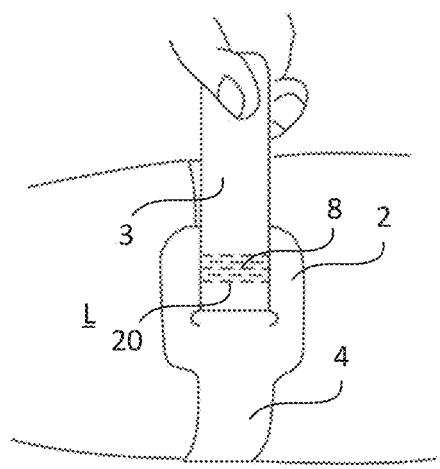
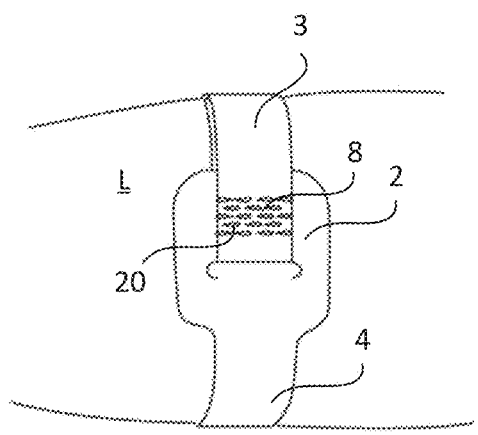
Fig. 5b    Fig. 5c

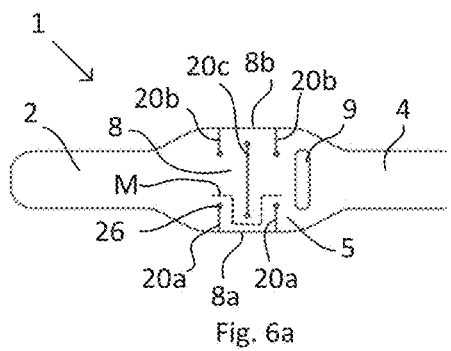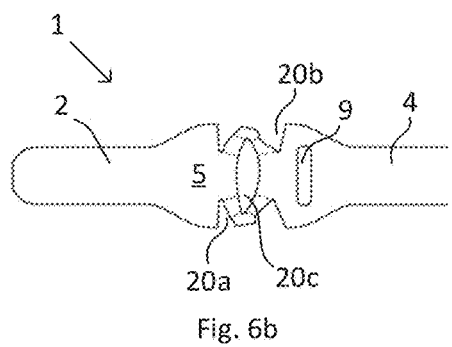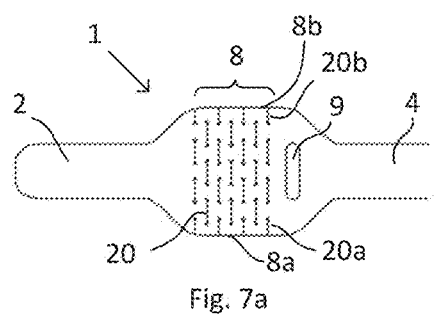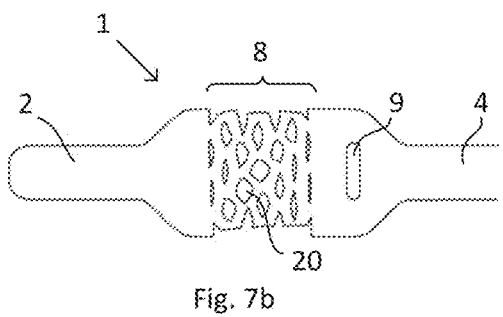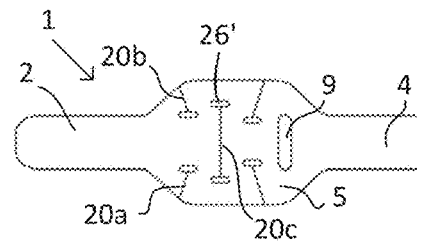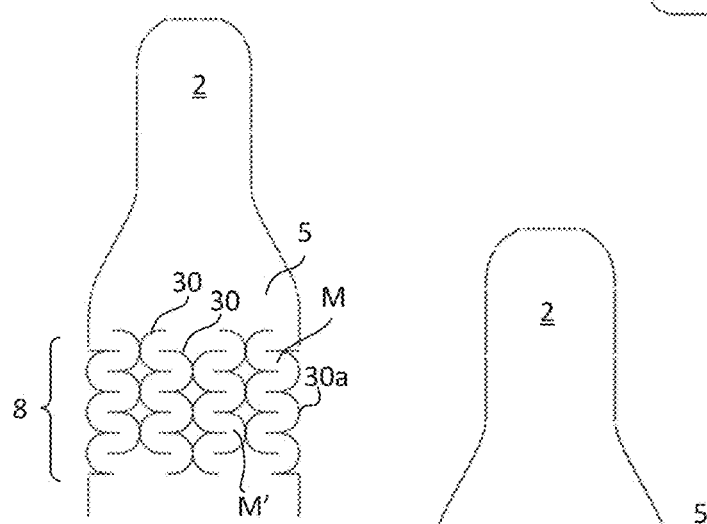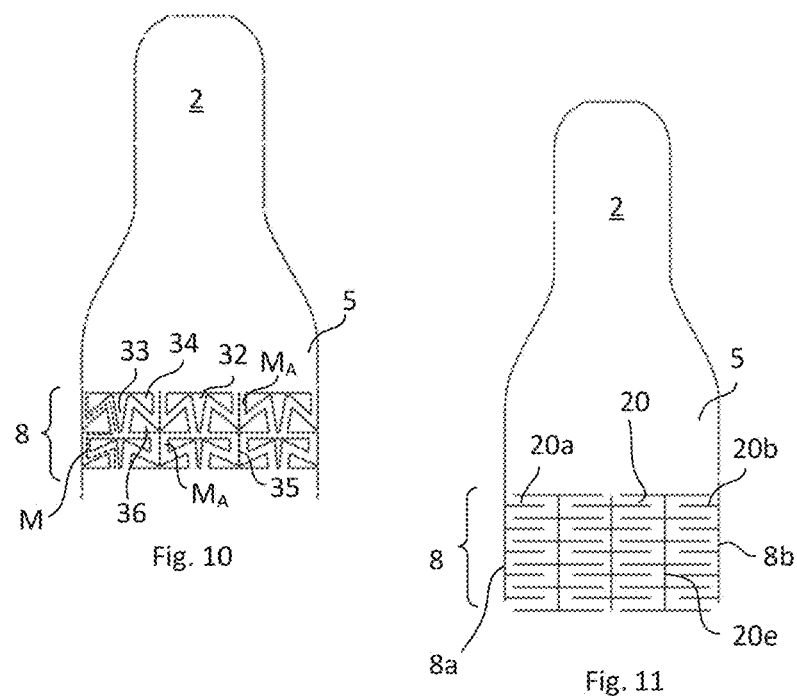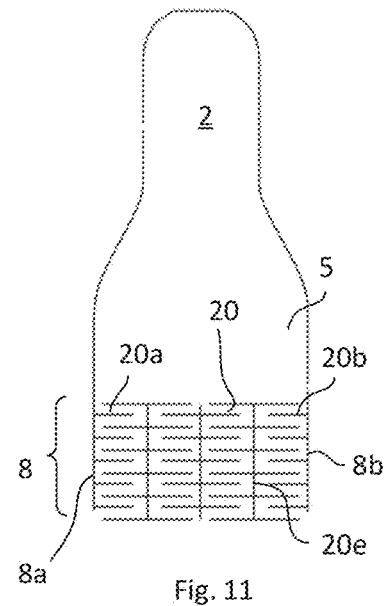

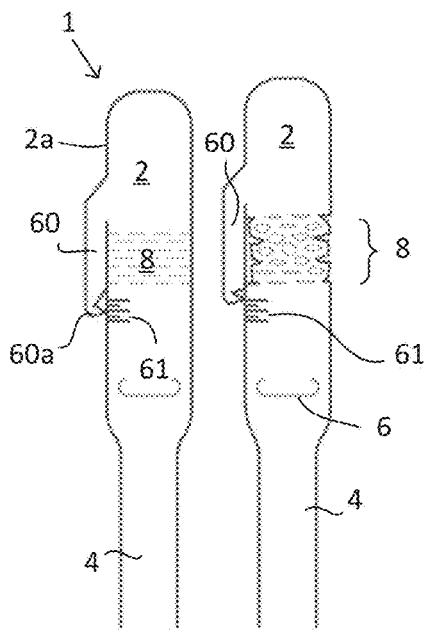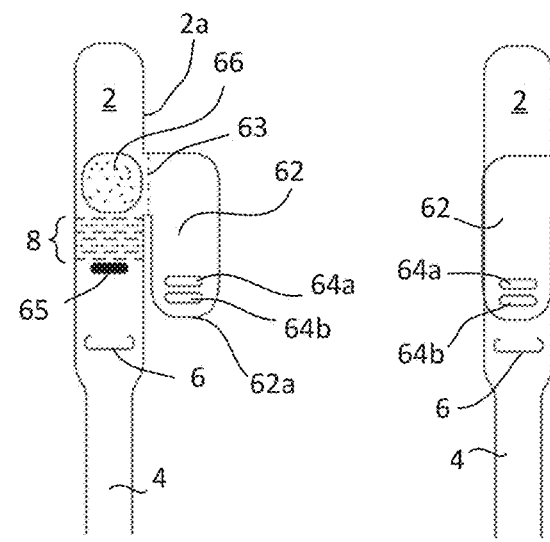
Fig. 18a  Fig. 18b
Fig. 19a  Fig. 19b
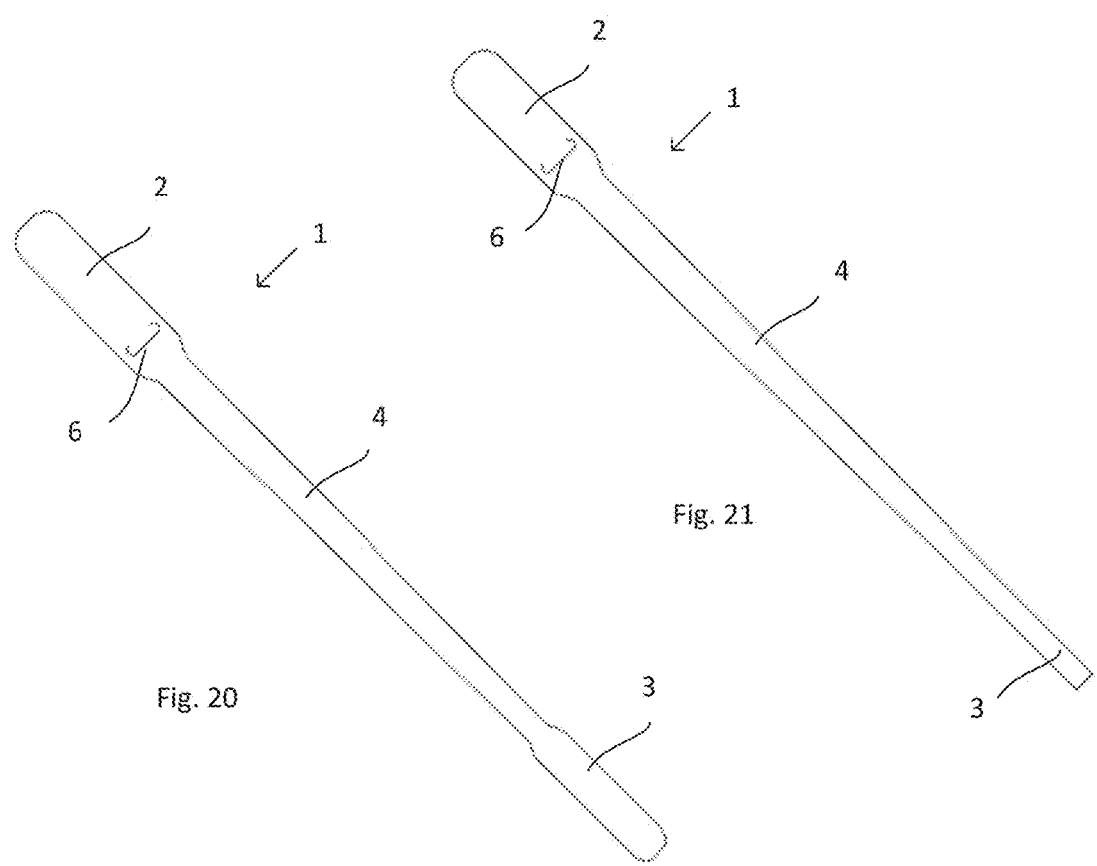
Fig. 20
Fig. 21

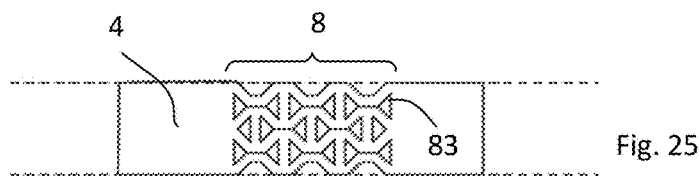
Fig. 25a
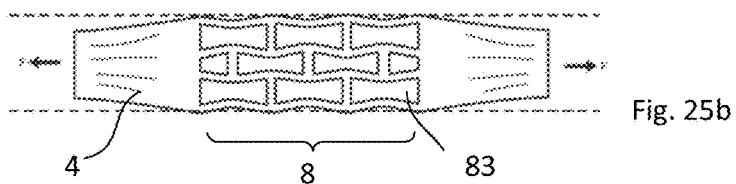
Fig. 25b
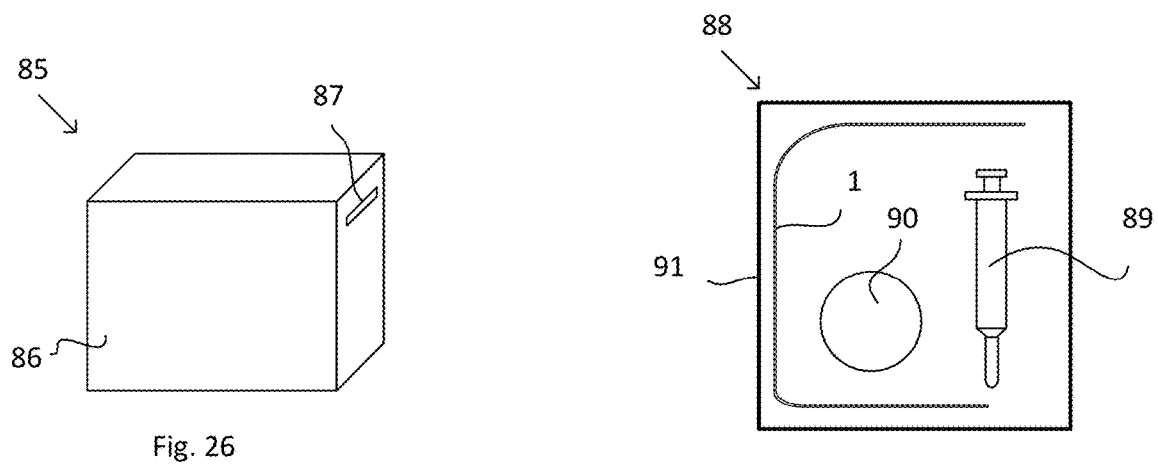
Fig. 26
Fig. 27
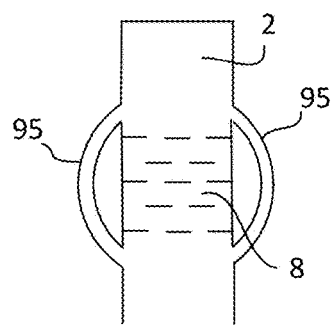
Fig. 28
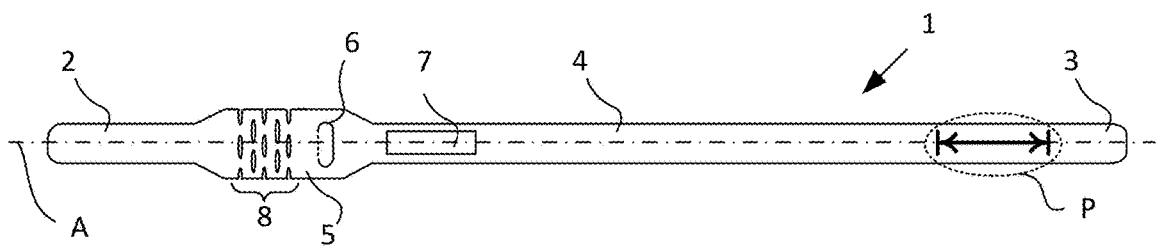
Fig. 29

TOURNIQUET

CROSS-REFERENCE TO RELATED APPLICATION

This application is a 35 U.S.C. § 371 national stage application of PCT Application No. PCT/SE2018/050744 filed on Jul. 6, 2018, entitled "TOURNIQUET," which claims priority to Swedish Patent Application No. 1700147-0 filed on Jul. 17, 2017, each of which are incorporated herein in their entirety by reference.

TECHNICAL FIELD

The present disclosure relates in general to a tourniquet, in particular a disposable tourniquet. The present disclosure further relates to a dispenser comprising a plurality of tourniquets, and a kit comprising a single tourniquet and at least one additional component.

BACKGROUND

Intravenous (IV) access is the most common invasive procedure in health care. Its purpose is to supply medication or to retrieve blood samples for laboratory tests. Despite being such a high frequency procedure, first access attempts often fail. There have been reports showing that up to every third attempt at insertion of peripheral vein catheters fail, and blood sampling attempts are likewise subject to failure, although less frequently. Failures can cause pain and increased risk of infection in patients, increase time until medication can be administered, can cause stress to both patient and clinician, expose clinicians to disease and cause significant loss of time and resources.

A tourniquet is used for example for restricting venous flow when attempting to gain intravenous access. The tourniquet is wrapped and tightened around an arm (or another limb) of a human or animal patient in order to distend the veins. This helps to facilitate the retrieval and puncture of a vein with a needle for extracting a sample of blood or effecting intravenous injection.

Various types of tourniquets are previously known. The perhaps most simple one is a rubber band simply tied around a body member. Others comprise a strip made of an elastic material and held in place by a fastener, such as a clamp. These tourniquets are generally configured to be reusable. Reusable tourniquets can spread microorganisms between patients and therefore pose a risk for infections being passed from one patient to another.

The problem associated with reusable tourniquets can of course be overcome by the use of disposable tourniquets. However, it is essential that the production cost for a disposable tourniquet is very low in order to be able to compete with the reusable tourniquets. Examples of disposable tourniquets can be found in EP 1,796,556 B1 and U.S. Pat. No. 5,219,356 A.

FIG. 1 illustrates a top view of a disposable tourniquet 100 according to prior art. The tourniquet 100 consists of a strip having a head portion 2 at a first longitudinal end of the strip, and a tail portion 3 at the opposing longitudinal end portion. The longitudinal central axis of the strip is denominated A in FIG. 1. The strip further comprises a loop portion 4 between the head portion 2 and the tail portion 3. The loop portion 4 is intended to be wrapped around a limb such as to encircle the limb. The strip further comprises an intermediate portion 5 with a greater width than the width of the loop portion 4 and the tail portion 3. The intermediate portion 5 is arranged between the head portion 2 and the loop portion. The intermediate portion 5 comprises a transverse cut 6 forming an opening through which the tail portion and possibly a part of the loop portion may pass. The strip further comprises an adhesive 7 on a part of the loop portion 4 adjacent the intermediate portion 5.

When the tourniquet 100 is to be used, the loop portion is arranged such as to encircle the limb of the patient, and the tail portion is threaded through the opening formed by the cut 6. Then the head portion and tail portion are pulled in opposite directions such as to tighten the tourniquet around the limb and thereby apply a compression force to the limb. Thereafter the tail portion, or a part of the loop portion, which has passed through the cut 6, is fastened to the loop portion in an overlapping manner by means of the adhesive 7 such that the compression force is maintained.

Many previously known tourniquets, such as the one shown in FIG. 1, suffers from the drawback of not providing means for knowing the pressure applied and/or not consistently providing the correct pressure to produce adequate distension of the veins to permit easy and accurate insertion of a needle. This leads to many unnecessary failed attempts of gaining intravenous access.

Attempts to solve the above-mentioned problems have been made. For example, US 2016/0287262 A1 discloses a venous tourniquet comprising a strap that can be placed around a body part. The strap comprises a tension indicator, with the use of which the tensile force in the strap, in the vicinity of or near the tension loop wrapped around the body part, can be detected by a user. The tension indicator is constructed by an element arranged over an elastic portion of the strap such that when not in use, the element is provided in a loop-shape. When the elastic portion is stretched to a defined length, the loop-shaped element limits further elongation of the strap and thereby provides information to the user that sufficient pressure has been achieved. This tourniquet however has the disadvantage of not compensating for different limb radii, resulting in the same force being applied to all limbs, regardless of physiology. Further, it relies on the necessary use of two materials having different properties and which need to be appropriately fastened to each other, which in turn may increase the cost of manufacturing the tourniquet.

US 2013/0304113 A1 discloses a disposable tourniquet in the form of a band of a thin, non-stretchable material arranged to be wrapped around a patient's limb, tightened and locked in place. The tourniquet also comprises means for controlling the amount of tension applied to the band when it is tightened about the limb of the patient. Said means comprises two flexible legs connecting a tab to be gripped by a user with the rest of the tourniquet. The flexible legs are adapted to be straightened out when the tab is pulled by the user, thereby moving an indicator (extending from the tab) in relation to a static portion, thereby indicating the amount of tension. This tourniquet also suffers from lack of compensation for limb circumference, and may also be sensitive to the direction of applied force as well as the skill of the user, thereby risking not providing consistent results.

SUMMARY

The object of the present invention is to provide a tourniquet that enables easy and reliable deduction that intended appropriate pressure is applied by means of the tourniquet when the tourniquet is employed and tightened around a limb. Furthermore, it should be possible to produce the tourniquet at low cost, such that it can be used as a disposable tourniquet.

The object is achieved by a tourniquet comprising a strip having longitudinal axis, a head portion at a first longitudinal end of the strip, a tail portion at a second longitudinal end of the strip, and a loop portion between the head portion and the tail portion, the loop portion having a sufficient length to encircle a limb of a human or animal. The strip further comprises a tension sensor having a longitudinal axis, a first longitudinal end and a second longitudinal end. The longitudinal central axis of the tension sensor preferably coincides with the longitudinal central axis of the strip. The tension sensor comprises a plurality of cuts arranged in a predetermined pattern, wherein the pattern forms at least one meandering path of strip material defined between individual cuts of the plurality of cuts, the meandering path extending from the first longitudinal end of the tension sensor to the second longitudinal end of the tension sensor. The plurality of cuts hinder a linear shortest available path through the material of the strip that links the first longitudinal end of the tension sensor and the second longitudinal end of the tension sensor. The tourniquet is preferably a disposable tourniquet.

The plurality of cuts are preferably arranged in the predetermined pattern in the tension sensor such that they define at least two meandering paths of strip material between the cuts as seen along the longitudinal axis of the tension sensor. The meandering paths each extend from one longitudinal end of the tension sensor to another longitudinal end of the tension sensor. The two meandering paths may be a mirror image of one another about the longitudinal central axis of the strip. This facilitates for tension force to be evenly distributed in the tension sensor upon application.

The tension sensor is adapted to enable a user to determine when an appropriate pressure is applied by means of the tourniquet to a limb on which the tourniquet is used.

More specifically, the tension sensor is adapted to extend along the longitudinal axis of the tourniquet by widening of the plurality of cuts, when the tourniquet is subjected to a tension force along its longitudinal axis. The material pattern resulting from the plurality of cuts provides a controlled resistance to the applied tension force and enables the user to determine when the intended appropriate tension in the tourniquet has been achieved, the tension force correlating to pressure on the limb to which the tourniquet is applied. Thereby, the tourniquet is easy to use and reliable information is received by the user with regard to the pressure applied during use. Furthermore, the tourniquet can easily be manufactured out of a sheet of material, such a sheet optionally comprising a plurality of layers, simply by cutting, stamping or the like if desired. By way of example, multiple tourniquets may be cut out simultaneously over the sheet surface, the tourniquets' longitudinal axes being arranged in parallel, side-by-side in a first axis of the sheet. This allows for concurrent excision, print and local material application across multiple tourniquets. This leads to low production costs, which is an important issue in the case of disposable tourniquets. The tourniquets may even be produced in a roll-to-roll process or the like, leading to the possibility of very high production yield.

The tension sensor may be arranged in a portion of the strip that is intended not to be in direct contact with the skin of the limb to which the tourniquet is applied during use of the tourniquet. In other words, the tension sensor may be arranged in a portion adapted to overlap another portion of the strip. This inter alia has the advantage of avoiding any risk of the skin providing a frictional force that may influence the capacity of the tension sensor to extend when subjected to a tension force applied by a user. Alternatively, the tension sensor may be arranged in a portion of the strip intended to be in direct contact with the skin of the limb, for example the loop portion.

The tension sensor further comprises a first longitudinal edge and a second longitudinal edge. A first cut of the plurality of cuts may suitably reach to the first longitudinal edge, and a second cut of the plurality of cuts may suitably reach to the second longitudinal edge. This may in certain cases facilitate the function of the tension sensor. It also has the advantage of a tourniquet that is easy to use.

The strip may comprise an indicium, or indicia, adapted to inform a user when a circumference of the limb is within an acceptable range necessary for applying an intended appropriate pressure to the limb corresponding to a tension force as determined by the tension sensor. This may for example be suitable when the tourniquet is intended for use only on limbs having a circumference within a specific range. Such an indicium may suitably be provided in the loop portion of the strip. Furthermore, such an indicium may suitably be intended to function with the intersection point of the strip, i.e. the point where the overlap of parts of the strip occurs when the tourniquet has been applied to the limb such as to apply a pressure on the limb.

The loop portion may suitably be configured for taking into account different limb circumferences in order to apply an intended pressure to the limb that is correlated to the applied tension force as determined by the tension sensor. Thereby, the tourniquet is not limited for use with a specific limb circumference or specific range of limb circumferences. The configuration of the loop portion so as to take into account different limb circumferences may be in the form of indicia, in the form of geometric configuration of the loop portion, or in the form of modification of constituent parts of the loop portion.

The strip may suitably be made of substantially inelastic material. This inter alia has the advantage that the width of the strip in the loop portion will not be altered during use of the tourniquet, which in turn improves the accuracy in obtaining the intended appropriate pressure on the limb.

The strip may further comprise an intermediate portion arranged between the head portion and the loop portion. The intermediate portion has a greater width than the width of the loop portion. This has for example the advantage of enabling the tension sensor to be arranged in such an intermediate portion if desired.

The strip may further comprise an opening configured for allowing the tail portion and optionally at least a portion of the loop portion, to pass through the opening. This for example allows the head portion and/or tail portion to overlap the loop portion. The opening is preferably an enclosed opening, meaning that the opening does not reach any longitudinal edges of the strip. The opening minimises the risk of unintended shear stress in the tension sensor when the tourniquet is subjected to a tension force along the longitudinal axis of the strip.

The plurality of cuts in the tension sensor may comprise a plurality of slits. Slits may be favourable compared to other forms of cuts such as holes as the formation thereof does not require any removal of material which in turn could lead to a reduction of strength of the strip material. The slits may however be provided with small rounded holes at their ends, if desired, so as to reduce the risk of sharp ends of the slits acting as initiation points for tear or break.

Some of the slits may suitably be oriented perpendicular to the longitudinal axis of the strip. This inter alia facilitates the intended widening of the slits when the tourniquet is subjected to tension. Optionally, all of the slits may be oriented perpendicular to the longitudinal axis of the strip. The slits that are oriented perpendicular to the longitudinal axis of the strip may suitably be arranged in a plurality of rows, each row comprising more than one slit.

The strip may comprise a first strip layer and a second strip layer superimposed on the first strip layer. In such a case, the tension sensor may suitably be arranged in the first strip layer. The first strip layer may suitably span over the whole longitudinal axis of the strip, whereas the second strip layer may span only a part of the longitudinal axis of the strip or over the whole longitudinal length of the strip. The presence of two strip layers facilitates for example the use of various forms of indicia for visually informing the user when the appropriate pressure has been achieved on the limb during use. Alternatively, or in addition, it may also provide the tourniquet with additional technical benefits in the form of its function.

The second strip layer may for example be divided along the transverse axis of the strip into two separate parts. This enables for relative movement of the two separate parts in relation to each other in response to extension of the tension sensor in the first strip layer. Thereby, it is for example possible to provide the second strip layer with indicia intended to form a desired shape only when the two separate parts of the second strip layer has been moved in relation to one another.

Alternatively, the second strip layer may comprise at least one perforation traversing from a first longitudinal edge of the second strip layer to a second longitudinal edge. The perforation may for example be intended to rupture when the tourniquet is subjected to a tension force along the longitudinal axis of the strip, said tension force applied by a user when pulling the tourniquet; the rupture of said perforation thereby effectively forming two separate parts of the second strip layer, as described above.

The second strip layer may also comprise a plurality of said perforation. The perforations are in such a case parallel to each other and are suitably oriented essentially perpendicular to the longitudinal axis of the strip. The second strip layer comprises a number of removable portions, each defined by two adjacent parallel perforations of the plurality of perforations. The first and second strip layer may be locally adhered to one another in the vicinity of said perforations. Furthermore, the first strip layer comprises a plurality of tension sensors arranged along the longitudinal axis of the loop portion, each tension sensor comprising a plurality of cuts arranged in a predetermined pattern wherein the pattern forms at least one meandering path, as described above. The tension sensors may have the same or different configurations. Each tension sensor is arranged below one of the removable portions of the second strip layer such that when one removable portion of the second strip layer is removed, the tension sensor arranged below the removed portion is rendered operable. The second strip layer ensures that the remaining tension sensors remain inoperable. Thereby, the user can easily select where an operable tension sensor may be arranged along the longitudinal axis of the loop portion.

At least a first tension sensor of the plurality of tension sensors in the first strip layer may have a different Young's modulus compared to a second tension sensor of the plurality of the tension sensors. The Young's modulus of an individual tension sensor may suitably be a function of the location of the individual tension sensor along the longitudinal axis of the strip in the loop portion. Thereby, it is possible to adjust the applied tension force so that it compensates for very different limb circumferences.

The loop portion may optionally have a width that tapers towards the tail portion. Thereby, appropriate intended pressure on the limb can be achieved irrespective of the limb circumference. For example, a limb of a child will be subjected to an average width of the loop portion which is greater than the average width of the loop portion that the limb of an adult is subjected to. Pressure exerted on the limb depends on both the tension in the strip as well as the surface area of the tourniquet that is in contact with the limb. Either or both these variables may be modified to provide a suitable pressure. A tourniquet comprising a loop portion with a width tapering towards the tail portion corrects the pressure applied using change to the surface area that the force is applied to, so that force correction is not necessary at the tension sensor.

The tourniquet may further comprise a pressure indicator element attached to the strip at a first side of the tension sensor as seen along the longitudinal axis of the strip. The pressure indicator element may be a separate constituent component of the tourniquet or be a part of the strip as such. The pressure indicator element is adapted to be of sufficient length to extend past the tension sensor as seen along the longitudinal axis of the strip such that a free end of the pressure indicator element is arranged on a second side of the tension sensor as seen along the longitudinal axis of the strip. Such a pressure indicator element may facilitate for the user to visually determine that an intended appropriate pressure has been achieved during use of the tourniquet. Due to the arrangement of the pressure indicator element, the free end of the pressure indicator element is moved in relation to the strip in response to the extension of the tension sensor.

The pressure indicator element may optionally be foldable about the strip such that, during use of the tourniquet, it is adapted to be arranged above or under the tension sensor. Alternatively, the pressure indicator element may be provided on a side of the strip, such as in the same plane as the strip. In these two cases the pressure indicator element may be attached to a longitudinal edge of the strip. Alternatively, the pressure indicator element is attached to a top surface of the strip such that it is superimposed on the strip while still having a free end.

The pressure indicator element may comprise an aperture configured to function with an indicium or indicia present on a surface of the strip to thereby visually inform the user when an intended appropriate pressure has been achieved. Alternatively, the free end of the pressure indicator element may be configured to function with an indicium or indicia on a surface of the strip to thereby visually inform the user when an intended appropriate pressure has been achieved.

In cases where the strip comprises an intermediate portion and the tension sensor is arranged in said intermediate portion, the plurality of cuts may be in the form of holes. These holes may preferably be configured to allow the tension sensor to obtain the same width as the adjacent loop portion and/or head portion when the intended tension force is applied. Thereby, the user is able to visually determine that the appropriate pressure on the limb has been achieved. Preferably, the head portion and the loop portion have the same width, which is smaller than that of the intermediate portion prior to tension application.

The strip may alternatively be made of an elastic material. In such a case, the loop portion contains a plurality of cuts that are provided in an auxetic pattern. The auxetic pattern compensates for, or controls, the reduction in width that occurs in an elastic material when stretched. The auxetic pattern may be a part of the tension sensor, or may be a separate constituent component of the strip different from the tension sensor.

The tourniquet may furthermore comprise an indicium or indicia associated with the tension sensor and adapted to visually illustrate when the intended pressure is exerted by the tourniquet. Such indicium or indicia may for example be in the form of a print in the tension sensor or in the vicinity thereof, or in the form of a thread or the like with high visibility, where the thread is incorporated into the tension sensor and adapted to change shape when the tourniquet is subjected to tension.

The tourniquet may further comprise at least one limitation member that is connected to a point on the first longitudinal edge of the strip, where this point is adjacent to the tension sensor, and also connected to a second point along the first longitudinal edge of the strip, were this second point is adjacent to the tension sensor and in a different location to the first point. The limitation member is configured to be straightened in response to the extension of the tension sensor when the tourniquet is subjected to a tension force. The limitation member may suitably be provided in the same plane as the strip. The limitation member has the purpose of ensuring that the tension sensor cannot be extended to such a length that it can cause discomfort or harm to the patient.

The tourniquet suitably further comprises means for fastening overlapping portions of the strip when the loop portion of the strip is encircling a limb such that it applies a pressure to the limb. Examples of means for fastening overlapping portions of the strip include, but are not limited to, adhesive as well as hooks and loops. This avoids the need for a separate component to be used for fastening overlapping portions of the strip when the tourniquet is used, thereby facilitating usage of the tourniquet and reducing cost.

The present invention also relates to an elongated continuous tourniquet band comprising a plurality of tourniquets as described above. In the elongated continuous tourniquet band, the tourniquets are detachably connected to one another at the longitudinal ends of the tourniquets. In other words, the tourniquets are arranged one after another along the longitudinal axis of the elongated continuous tourniquet band such that the longitudinal central axis of each tourniquet coincides with the longitudinal central axis of the tourniquet band, and the tourniquets are detachably connected to each other. Thereby, an individual tourniquet can easily be retrieved from the band when it is intended to be used.

The present invention also relates to a dispenser comprising a housing and an elongated continuous tourniquet band as described above. The elongated continuous tourniquet band may be in the form of a roll or arranged in a zigzag arrangement, and is packaged inside the housing. The housing comprises an opening from which the elongated continuous tourniquet band can be drawn out to reveal a tourniquet one at a time for separation from the remainder of the elongated continuous tourniquet band. The housing may suitably be a sterile housing, if needed.

The present invention furthermore relates to a kit comprising a package that may be sterile, a tourniquet as disclosed above and at least one additional component. The tourniquet and the additional component or additional components, of which there is at least one, are provided in the package. Examples of additional components include a syringe, a pair of gloves, a tray, a swab adapted for disinfection, one or more absorption swabs, flush syringe, dressing, gauze sponges, specimen bag, adhesive bandage, tape, one or more blood collection tubes, bottle of alcohol, one or more swab sticks, pen, one or more antiseptic wipes such as alcohol pads, surgical or face mask, IV tubing extension set, some form of medicament such as an analgesic, and paper cloth. Such a kit may replace previously known kits currently used in clinics. Furthermore, such a kit may for example be especially suitable for use in the field, for example in an ambulance, in a war zone, or in a zone of natural disaster.

The tourniquet according to the present invention is primarily intended to be used for applying compression to parts of the body of a human or animal to aid intravenous access.

BRIEF DESCRIPTION OF DRAWINGS

FIG. 4a illustrates a top view of a part of a tourniquet according to a third exemplifying embodiment, before being subjected to tension.

FIG. 4b illustrates a top view of the tourniquet according to FIG. 4a when subjected to tension.

FIG. 5a illustrates a perspective view of a tourniquet according to a fourth exemplifying embodiment, when wrapped around a limb but before being subjected to tension.

FIG. 5b illustrates a perspective view of the tourniquet according to FIG. 5a during start of pulling the tourniquet wrapped around a limb.

FIG. 5c illustrates a perspective view of the tourniquet according to FIG. 5a when subjected to the intended tension force and fastened with the tension force retained.

FIG. 6a illustrates a top view of a part of a tourniquet according to a fifth exemplifying embodiment before being subjected to tension.

FIG. 6b illustrates a top view of the tourniquet according to FIG. 6a when subjected to tension.

FIG. 7a illustrates a top view of a part of a tourniquet according to a sixth exemplifying embodiment before being subjected to tension.

FIG. 7b illustrates a top view of the tourniquet according to FIG. 7a when subjected to tension.

FIG. 8 illustrates a top view of a part of a tourniquet according to a seventh exemplifying embodiment before being subjected to tension.

FIG. 9 illustrates a top view of a part of a tourniquet according to an eight exemplifying embodiment before being subjected to tension.

FIG. 10 illustrates a top view of a part of a tourniquet according to a ninth exemplifying embodiment before being subjected to tension.

FIG. 11 illustrates a top view of a part of a tourniquet according to a tenth exemplifying embodiment before being subjected to tension.

FIG. 18a illustrates a top view of a part of a tourniquet according to a seventeenth exemplifying embodiment before being subjected to tension.

FIG. 18b illustrates a top view of the tourniquet according to FIG. 18a when subjected to tension.

FIG. 19a illustrates a top view of a part of a tourniquet according to an eighteenth exemplifying embodiment before being subjected to tension, where a foldable pressure indicator element flap has not been folded over the tension sensor.

FIG. 19b illustrates a top view of the tourniquet according to FIG. 19a before being subjected to tension, but wherein the foldable pressure indicator element flap has been folded over the tension sensor.

FIG. 20 illustrates a top view of a tourniquet according to a nineteenth exemplifying embodiment before being subjected to tension.

FIG. 21 illustrates a top view of a tourniquet according to a twentieth exemplifying embodiment before being subjected to tension.

FIG. 24b illustrates a top view of the tourniquet according to FIG. 24a.

FIG. 25a illustrates a top view of a part of a tourniquet according to a twenty-fourth exemplifying embodiment before being subjected to tension.

FIG. 25b illustrates a top view of the tourniquet according to FIG. 25a when subjected to tension.

FIG. 26 illustrates a perspective view of a dispenser according to one exemplifying embodiment.

FIG. 27 illustrates a top view of a kit according to one exemplifying embodiment.

FIG. 28 illustrates a top view of a part of a tourniquet according to twenty-fifth exemplifying embodiment before being subjected to tension.

FIG. 29 illustrates a top view of a tourniquet according to a twenty-sixth exemplifying embodiment before being subjected to tension.

DETAILED DESCRIPTION

Figure 1:
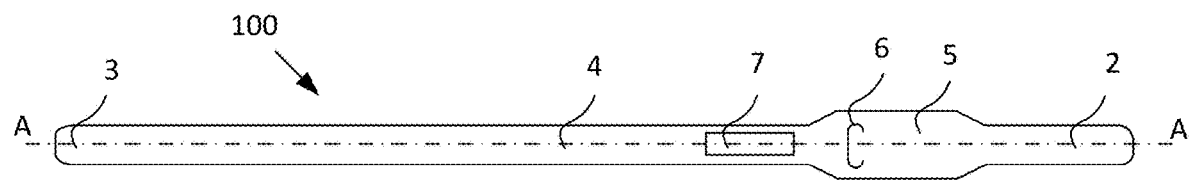
FIG. 1 illustrates a top view of a tourniquet according to prior art.

The present invention will be described below with reference to the accompanying drawings and certain exemplifying embodiments. The invention is however not limited to the embodiments shown, but may be varied within the scope of the appended claims. Moreover, the drawings shall not be considered to necessarily be drawn to scale as some features may be exaggerated in order to more clearly illustrate the features of the device(s) or the details thereof.

A tourniquet shall in the present disclosure be considered to mean a device configured for restricting and/or arresting the flow of blood through a vein or artery by compressing a limb.

Furthermore, in the present disclosure, the term "disposable tourniquet" shall be considered to mean as intended for use only one time. It should however be recognised that the tourniquet may be used more than one time, if desired. It is however not intended for multiple use, such as for more than one patient.

Moreover, in the present disclosure, the term "sensor" is used for the purpose of describing a device configured to respond to physical stimuli and provide resulting information regarding the physical stimuli. Thus, the term "tension sensor" is in the present disclosure considered to mean a device configured to respond to a physical stimuli in the form of tension and to provide information relating to said tension to a user. The information regarding the tension may be provided to the user by his or her visual inspection of the tension sensor.

Furthermore, in the present disclosure, the term "cut" shall be interpreted broadly and encompasses any form of through-extending opening, such as a slit, slot, perforation, hole, aperture etc.

The term "meandering path" is in the present disclosure used in conjunction with the description of features of the tension sensor, more specifically in relation to the pattern of the plurality of cuts in the tension sensor. In the present disclosure, the term "meandering" shall be considered as something that advances or proceeds by taking a winding or indirect course in respect to a certain direction, such that the course alters with respect to the direction at least once. The term "meandering path" should therefore be considered to encompass for example a path having a sinusoidal or serpentine course, a square-shaped sinusoidal course, a zig-zag shaped course, a trapezoid-shaped sinusoidal course, a jigsaw-shaped course, etc.

Moreover, the term inelastic is used in the present disclosure when describing a material property. It should however be noted that no material is truly inelastic. Therefore, in the present disclosure, the term "substantially inelastic" is used. A substantially inelastic material shall be considered to mean a material which is not elongated at a tension force capable to be achieved by a human pulling the material in the plane of the material, assuming that the material is free from any cuts, macroscopic defects or the like.

The tourniquet according to the present invention is designed to inform a user when an intended tension of the tourniquet has been achieved during pulling the tourniquet during use. The intended tension of the tourniquet is correlated to the intended pressure exerted on the body part around which the tourniquet is applied.

The tourniquet according to the present invention comprises a strip having a head portion at a first longitudinal end of the strip, which suitably may be intended to be gripped by the user for pulling the tourniquet when the tourniquet has been wrapped around a body part, in particular a limb, for applying pressure thereto. The strip further comprises a tail portion at a second longitudinal end of the strip. The tail portion may be gripped by a user for pulling the tourniquet when the tourniquet has been wrapped around a body part such that the tourniquet encircles the body part. The strip also comprises a loop portion arranged between the head portion and the tail portion, the loop portion having a sufficient length to encircle the body part, in particular a limb. At least one of the head portion and the tail portion is intended to not be in direct contact with the skin of the limb of the patient during use of the tourniquet, but merely overlap with the loop portion. The tourniquet may further comprise an intermediate portion, which may or may not have a greater width than the loop portion, if desired. Such an intermediate portion would in such a case be arranged between the head portion and the loop portion. Moreover, the strip may comprise an opening intended to allow for the tail portion, and possibly a part of the loop portion, to pass through during use. Such an opening may suitably be formed by a substantially transverse cut. Moreover, said opening may suitably be arranged in the intermediate portion or in the head portion. Furthermore, the tourniquet may comprise an adhesive intended for fastening the tourniquet when the appropriate pressure has been achieved (for example, compare to the adhesive 7 shown in FIG. 1). Alternatively, the tourniquet may suitably comprise some other means for fastening overlapping parts of the tourniquet when the tourniquet has been wrapped around the limb of a patient. Any previously known fastening means may be used, for example hooks and loops.

The tourniquet according to the present invention may consist solely of the strip, or comprise the strip and at least one further constituent component.

In contrast to the prior art shown in FIG. 1, the tourniquet according to the present invention further comprises a tension sensor intended to inform the user that the appropriate and intended tension in the tourniquet, and hence the intended pressure on the body part, has been achieved. The tension sensor suitably has a longitudinal axis coinciding with the longitudinal axis of the strip. Alternatively, the tension sensor may have a longitudinal axis that is parallel to the longitudinal axis of the strip. Furthermore, the tension sensor has a width defined by a first longitudinal edge and a second longitudinal edge. The longitudinal edges thus form outer edges of the tension sensor. The first and second longitudinal edges may be parallel, but the invention is not limited thereto. In other words, the width of the tension sensor may be constant along the longitudinal axis of the tension sensor or may vary along the longitudinal axis of the tension sensor, such as tapering, comprising a thicker midsection, et c. In any case, the first longitudinal edge and the second longitudinal edge of the tension sensor are a mirror image of one another along the central longitudinal axis of the tension sensor, i.e. a mirror image of one another with respect to a central longitudinal axis of the strip. A longitudinal extension of the tension sensor is in the present context considered to be along the same axis as the longitudinal axis of the strip. The tension sensor may suitably have the same width as the width of the strip in the portion of the strip where the tension sensor is arranged. It is however also plausible that the width of the tension sensor is different than the width of the strip, and both narrower and greater widths are plausible.

The tension sensor comprises a plurality of cuts arranged in a predetermined pattern. The pattern may optionally comprise a plurality of different sub-patterns. The cuts are capable of widening along the longitudinal axis of the strip when the tourniquet is subjected to a pulling force along its longitudinal axis. The pattern of the plurality of cuts forms at least one meandering path of material, the meandering path being defined between individual cuts of the plurality of cuts. The meandering path extends from the first longitudinal end of the tension sensor to the second longitudinal end of the tension sensor. The meandering path meanders in respect to the longitudinal axis of the strip and in the plane of the strip. In other words, the course of the meandering path of the tension sensor alters at least once, preferably a number of times, along the longitudinal axis of the tension sensor. Thus, the tension sensor is capable of being extended along the longitudinal axis of the strip when the tourniquet is subjected to a pulling force. It should be recognised that the meandering path may comprise a portion thereof having a course which coincides with the longitudinal axis of the strip, at least when the strip is subjected to tension along the longitudinal axis.

In case the pattern comprises a plurality of different sub-patterns, these sub-patterns may be separated from each other along the longitudinal axis and/or along the transverse axis of the tension sensor. In case of their being separated from each other along the transverse axis, they are suitably separated by one or more straight cuts that are oriented parallel to or along the longitudinal axis.

A meandering path constitutes the shortest available path through the strip material from a point at the first longitudinal end of the tension sensor to the second longitudinal end of the tension sensor.

In order for the tension sensor to elongate along the longitudinal axis upon being subjected to a tension force directed along the longitudinal axis of the tension sensor, this shortest available path must be longer than the linear distance between the first and second longitudinal ends of the tension sensor in its relaxed state prior to extension. This is achieved by the plurality of cuts that hinders a linear shortest available path in the longitudinal direction of the tension sensor through the strip material that links the first and second longitudinal ends of the tension sensor when the tension sensor is in its relaxed state prior to being subjected to a tension force during use. Upon application of a tension force, the meandering path may partly or fully alter course as a result of said applied tension. In certain embodiments, the tension sensor may even elongate along the longitudinal axis such that a meandering path of the tension sensor becomes linear, i.e. parallel to the longitudinal axis of the strip, when the tension sensor is fully extended.

Suitably, the pattern forms a plurality of meandering paths. The meandering paths may be identical and arranged side by side as seen along the transverse axis of the tension sensor, i.e. being parallel. However, preferably, the meandering paths may be a mirror image of one another as seen along the longitudinal axis of the tension sensor. Furthermore, in case the plurality of cuts is arranged in a predetermined pattern that consists of a plurality of sub-patterns (of which at least two are different from each other), the meandering paths need not necessarily have the same length.

The plurality of cuts arranged in the predetermined pattern provides the tension sensor with an elasticity that is different to the elasticity of the remaining part of the strip. Furthermore, the predetermined pattern of the tension sensor may be configured such that it, upon applied tension force that exceeds the tension force that corresponds to the intended pressure to be applied to the limb by means of the tourniquet, may extend further than the extension achieved by the tension sensor when tension force is applied that corresponds to the intended pressure. Upon removal or reduction of the tension force, the elasticity of the tension sensor may allow the tension sensor to contract to shorter extension.

Preferably, at least a first cut of the plurality of cuts of the tension sensor reaches to the first longitudinal edge, and at least a second cut of the plurality of cuts of the tension sensor reaches to the second longitudinal edge. Suitably, more than one cut reaches to the first longitudinal edge of the tension sensor, and more than one cut reaches to the second longitudinal edge of the tension sensor. The tension sensor is however free from any cut reaching between both longitudinal edges of the tension sensor, since the sensor in such a case would break or otherwise fail.

Suitably, the cuts in the tension sensor are provided in a pattern which comprises a pattern unit which is repeated both along the longitudinal axis of the tension sensor and along the transverse axis of the tension sensor. While repeated, the pattern units may have different sizes in different parts of the tension sensor. Alternatively, the pattern units may have the same size throughout the tension sensor.

Tensile stress may cause movement within a sensor pattern. This movement may be in the direction of the applied tension, in the opposite direction of applied tension, perpendicular to applied tension or a combination that brings about resultant motion that is neither along the tension force or perpendicular to it. One or more indicators may be used within the sensor pattern, and their inter-related movement may bring about tension information. An indicator may for example be indicia incorporated in the tension sensor or in the vicinity thereof, and/or a pressure indicator element associated with the tension sensor. The function of having several indicators could be, in addition to showing the applied pressure, to show if shear stress is being caused, which would allow the user to stop shear stress and instead increase tension applied along the longitudinal axis of the tourniquet.

The strip may suitably be made of a substantially inelastic material. This has the benefit of easy control of the tension force along the longitudinal axis, and in the plane of the strip. The material must however be flexible enough to be able to be wrapped tightly around a limb without any crinkling or similar undesirable distortion. Examples of suitable inelastic material include, but are not limited to, paper or paper-based materials, plastic materials or the like. The strip may be made of any previously known substantially inelastic material used for the same purpose. Since tourniquets are exposed to patient fluids, including blood, tourniquets are discarded and burnt; they are not recycled. Therefore it is environmentally advantageous to source product material from renewable natural resources. For environmental purposes, the strip is preferably made of a paper-based material, a biodegradable plastic material, or a composite material comprising wood derived fibres and biodegradable fibres.

Alternatively, the strip may be made of a material having a positive Poission ratio, if desired. Such a strip may be paired with a tension sensor that has the same Young's modulus as the strip, so that applied tension may be quantized. The sensor pattern and the pressure indicator element associated with the sensor pattern would suitably be made to account for any change to band width incurred by the elastic material's Poisson ratio, which would cause higher local pressure.

Applied pressure by means of a tourniquet depends on the normal force onto a body surface and the area of the surface that the force is applied to. Force is in accordance with the present invention controlled by means of the tension sensor. The area corresponds to the surface area of the tourniquet in the loop portion encircling the limb, i.e. the area in direct contact with the limb. While a substantially inelastic material in the loop portion ensures a substantially constant width of the strip irrespective of applied tension force, limb circumference is variable across humans and animals and must therefore be accounted for in order to apply the pre-determined pressure. The present invention may take limb circumference into account in different ways, including
  i. Controlling for allowed limb circumference;
  ii. Modification of the force used in relation to the circumference of the limb; and/or
  iii. Modification of local width in the loop portion to match limb circumference.

These alternative ways to account for circumference of the limb will be evident from the exemplifying embodiments illustrated below.

By way of example, controlling for allowed limb circumference as given in (i.) above may suitably be made by instructing the user as to which circumference of a limb the tourniquet may be used on. This could for example be made by marking the tourniquet as such or the packaging thereof. Such a marking may if desired be combined with indicia associated with the tension sensor. Alternatively, controlling for allowed circumference as given in (i.) above may suitably be made by selecting an appropriate length of the loop portion. Thereby, it is ensured that the tourniquet may not be used for limbs having a greater circumference since it cannot be wrapped fully around such limbs.

By way of example, modification of the force used in relation to the circumference of the limb may be achieved by modifying the pattern of the plurality of cuts and the associated pattern variables, as well as the geometrical configuration of the cuts. Alternatively, or in addition, the selection of material may be modified or locally reinforced by a coating or other reinforcement.

By way of example, modifying the local width in the loop portion may comprise a tapered width of the loop portion towards the tail portion, or a narrower width in a part of the loop portion to apply a locally higher pressure by means of said part.

Tension sensor material and width may optionally vary from the rest of the tourniquet to ensure functionality. Alternate materials, or use of the same material at different density or thickness, or local application of additional material such as a polymer based coating or the like, can ensure part functionality independent of adjacent parts.

However, preferably, the tension sensor may suitably be made of the same material as the strip. In fact, the tension sensor may be achieved by simply providing the strip with the plurality of cuts in the predetermined pattern in a predetermined part of the strip. This reduces manufacturing costs and thus enables a low cost of the tourniquet, which is essential in the case of disposable tourniquets.

Figure 2A:
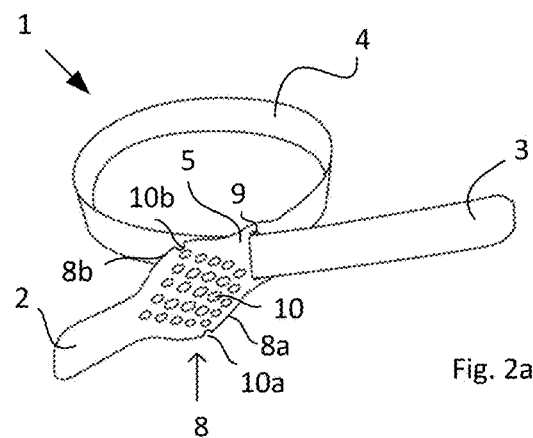
FIG. 2a illustrates a perspective view of a tourniquet according to a first exemplifying embodiment of the present invention.
Figure 2B:
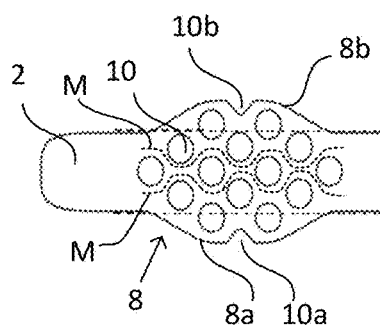
FIG. 2b illustrates a top view of a part of the tourniquet according to FIG. 2a before being subjected to tension.
Figure 2C:
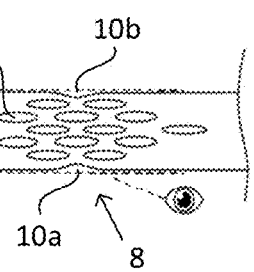
FIG. 2c illustrates a top view of a part of the tourniquet according to FIGS. 2a and 2b, when subjected to tension.

A first exemplifying embodiment of the tourniquet according to the present invention is illustrated in FIGS. 2a to 2c. FIG. 2a is a perspective view of the tourniquet 1 when the tail portion 3 and a part of the loop portion 4 have been passed through an opening 9 in an intermediate portion 5 of the strip, but before the tourniquet has been pulled to cause the intended compression on a body part (not shown). In other words, FIG. 2a shows the tourniquet before it has been subjected to a tension force. FIGS. 2b and 2c shows a top view of a part of the tourniquet 1, wherein FIG. 2b shows a view before the tourniquet is subjected to tension, i.e. in a relaxed state before use, and FIG. 2c shows the tourniquet when the tourniquet has been subjected to a tension force along the longitudinal axis of the strip by pulling the longitudinal ends of the strip in substantially opposite directions.

The tourniquet 1 comprises a strip having a head portion 2, an intermediate portion 5, a loop portion 4 and a tail portion 3. Furthermore, the strip comprises a tension sensor 8 arranged between the intermediate portion 5 and the head portion 2. The tension sensor 8 comprises a number of cuts in the form of holes 10, such as circular holes. The holes 10 are arranged in a predetermined pattern. In the pattern, the holes are repeated both along the longitudinal axis of the tension sensor and along the transverse axis of the tension sensor. The pattern of holes forms meandering paths of material defined between individual holes, the meandering paths extending from the first longitudinal end of the tension sensor to the second longitudinal end. In FIG. 2b, two of the meandering paths are indicated by means of the dotted lines M and have a substantially a sinusoidally shaped configuration. The indicated meandering paths of FIG. 2b are a mirror image of one another along the longitudinal axis of the strip. The holes are capable of widening along the longitudinal axis of the strip as shown in FIG. 2c. The holes may have the same size throughout the tension sensor, or have different sizes depending on the location of the respective holes in the pattern of holes. For example, the size of the holes may be provided in a gradient along the longitudinal axis of the tension sensor. Furthermore, the holes are arranged in the pattern such that a linear shortest available path of material, from one longitudinal end of the tension sensor 8 to an opposing longitudinal end of the tension sensor, does not exist when the tension sensor is in its relaxed state (i.e. before being subjected to a tension force applied by a user). A linear path in the strip material may however appear upon extension of the tension sensor by application of tension force.

As shown in FIGS. 2a-2c, a first hole 10a of the plurality of holes 10 may reach to a first longitudinal edge 8a of the tension sensor 8. Furthermore, a second hole 10b of the plurality of holes 10 may reach to a second longitudinal edge 8b of the tension sensor 8. It is however not necessary that there are any holes reaching to the longitudinal edges of the tension sensor, as long as a meandering path is obtained. The longitudinal edges 8a and 8b are in this exemplifying embodiment not parallel to each other before the tourniquet is subjected to a tension force, but may suitably be a mirror image of one another along the longitudinal axis of the strip as shown in FIG. 2b. When the tourniquet 1 has been wrapped around a limb and the tail portion has been allowed to pass through the opening 9, the user pulls the head portion 2 and the tail portion 3 in opposite directions, thereby tensioning the loop portion 4 around the limb of the patient. When further pulled, the tension sensor 8 is activated and the holes 10 widen such that the longitudinal length of the tension sensor 8 is increased. As is evident from the FIGS. 2a-2c, the tension sensor is arranged such that, during use of the tourniquet, this version of the tension sensor is not in direct contact with the limb to which the tourniquet is applied but in a portion overlapping another portion of the strip. In this particular embodiment, the tension sensor 8 is designed such that when the intended tension, and pressure is obtained, the width of the tension sensor conforms to the width of the head portion 2 as shown in FIG. 2c, thereby informing the user that the appropriate tension has been achieved. The user may then lock the tourniquet to retain the pressure by means of conventional fastening means, such as the adhesive as described with reference to FIG. 1.

Figure 3:
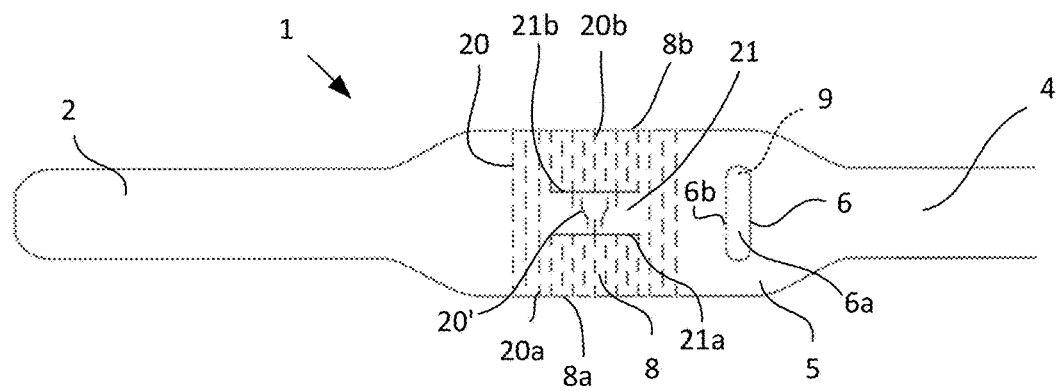
FIG. 3 illustrates a top view of a part of a tourniquet according to a second exemplifying embodiment of the present invention before being subjected to tension.

FIG. 3 illustrates a top view of a part of a tourniquet 1 according to a second exemplifying embodiment of the present invention. The tourniquet 1 comprises an intermediate portion 5 between the head portion 2 and the loop portion 4, the intermediate portion comprising an opening 9 adapted for passing the tail portion through it such that it overlaps with the loop region 4 during use. The opening may be achieved by a cut 6, creating a flap 6a which may be opened around a transverse fold 6b acting as a hinge for the flap 6a. The intermediate portion 5 further comprises the tension sensor 8. Thus, during use of the tourniquet, the tension sensor 8 will not be in direct contact with the limb to which the tourniquet is applied. In this exemplifying embodiment, the tension sensor 8 comprises a plurality of cuts arranged in a predetermined pattern, wherein the cuts are in the form of transverse slits 20. The slits 20 are patterned in a plurality of rows oriented perpendicular to the longitudinal axis of the strip, each row comprising a plurality of slits. The slits in a first row is somewhat offset to the slits of an adjacent row such that the joining material forms a meandering connection along the longitudinal axis of the tension sensor, in other words a meandering path of material. A meandering path of material defined by individual slits may be considered to have a square-sinusoidal shape.

Furthermore, at least a first slit 20a of the plurality of slits 20 reaches to a first longitudinal edge 8a of the tension sensor 8. Moreover, at least a second slit 20b reaches to the second longitudinal edge 8b of the tension sensor 8. The fact that there are slits reaching to the longitudinal edges ensures that the tension sensor can be operated despite that it has the same width as the remaining part of the intermediate portion. If no cuts would reach out to the longitudinal edges when the tension sensor has the same width as adjacent parts of the strip, the tension sensor would not be capable of being extended as there would be a string of material along the longitudinal edges of the tension sensor counteracting the extension of the tension sensor. It should also be noted that the first slit 20a does not reach to the second longitudinal edge 8b, and the second slit 20b does not reach the first longitudinal edge 8a.

As shown in FIG. 3, the tension sensor 8 may further optionally comprise a central portion 21 delimited by two longitudinal cuts 21a, 21b. The central portion 21 comprises a different pattern of cuts 20' than the other part of the tension sensor 8. The purpose of the central portion 21 may for example be to comprise indicia for enabling to visually determine whether the intended tension has been achieved during pulling of the tourniquet.

FIG. 4a illustrates a top view of a part of a tourniquet according to a third exemplifying embodiment before being subjected to a tension force, i.e. the tourniquet is in a relaxed state before use. The exemplifying embodiment shown in FIG. 4a is similar to the exemplifying embodiment of FIG. 3, except that it does not comprise an intermediate portion but a head portion 2 having a greater width than the loop portion 4. Furthermore, the tourniquet shown in FIG. 4a comprises a printed indicia suitably consisting of three lines 25a, 25b, 25c each printed on a separate part of the central portion 21, the parts separated by the cuts 20' (compare to FIG. 3). Two of the printed lines 25a, 25c are provided in along the same longitudinal line, and a middle line 25b is provided along a line which is parallel to the longitudinal line of the two peripherally printed lines 25a, 25c.

FIG. 4b illustrates the tourniquet according to FIG. 4a when subjected to a tension force in the longitudinal axis of the tourniquet. As shown in the figure, the tension force causes the cuts 20 to widen along the longitudinal axis, which causes the tension sensor 8 to obtain a greater length along the longitudinal axis compared to the relaxed state shown in FIG. 4a. Furthermore, when the intended tension force has been achieved, the three lines 25a, 25b, 25c of the printed indicia aligns to a single line 25, thereby providing the user with information that the appropriate pressure on the body part has been achieved. Thereafter, the user may fasten overlapping portions of the tourniquet to each other in accordance with conventional means, while maintaining the intended pressure on the body part.

FIGS. 5a to 5c illustrate a tourniquet 1 according to a fourth exemplifying embodiment and how the tourniquet is used. In the fourth exemplifying embodiment, the tension sensor 8 is arranged in the tail portion 3 of the strip. This is particularly suitable when it is desired to enable pulling the tourniquet with only one hand. As will be apparent from the below text and FIGS. 5a to 5c, the tension sensor will, during use of the tourniquet, not be in direct contact with the limb L.

FIG. 5a illustrates the tourniquet 1 when the loop portion 4 has been wrapped around a limb L, such as an arm, thereby encircling the limb L. Furthermore, the tail portion has been passed through an opening provided in the head portion 2 of the strip, but has not yet been subjected to any tension. The head portion 2 has a greater width than the tail portion and the loop portion such that the opening 9 is sufficiently wide for enabling the tail portion to pass through the opening 9. Moreover, the tail portion comprises an adhesive 7 for enabling the tail portion to be fastened to the loop portion after the appropriate tension has been achieved in the loop portion to apply the intended pressure to the limb L. The adhesive 7, suitably covered by a protective liner prior to use, is suitably arranged in the tail portion between the longitudinal end of the strip (at the tail portion) and tension sensor 8. The tension sensor 8 is in FIGS. 5a to 5c shown as a tension sensor comprising a plurality of cuts in the form of slits arranged in a plurality of rows. However, the tension sensor may comprise cuts arranged in a pattern in any configuration as described in the present disclosure.

FIG. 5b illustrates the tourniquet of FIG. 5a at the start of the pulling in the tail portion with the purpose of achieving an appropriate pressure to the limb L. At this stage, the cuts 20 have not yet started to widen. In other words, the tension sensor 8 has not yet been activated. When the user continues to pull the tourniquet in its tail portion, the tension sensor will be activated and the cuts will start to widen, thereby extending the tension sensor. Indicia (not shown) associated with the tension sensor may be provided to inform the user when the appropriate tension has been achieved and the tail portion can be fastened to the loop portion by means of the adhesive so as to maintain the tension achieved. FIG. 5c illustrates the tourniquet when tail portion 3 has been fastened by means of the adhesive 7 (see FIG. 5a), to the loop portion 4 where the tail portion overlaps the loop portion. As can be seen from FIG. 5c, the fact that the adhesive is provided between the longitudinal end of the strip and the tension sensor ensures that the tension sensor maintains the tension even after the tail portion has been fastened to the loop portion despite the fact that the user no longer is providing any pulling force. Thereby, the user can see the tension sensor and indicia associated therewith, and thus verify that the intended pressure has been achieved and is maintained, even after overlapping portions of the strip have been fastened. In the event that retention of a specific pressure is necessary for a prolonged period of time, the sensor pattern may also itself be adhesive and constitute the lock. The locked band then remains inextensible, which is useful if the Young's modulus of the sensor pattern is a function of wear and abrasion, in which case it would be at risk of extension over time, thus lowering the pressure exerted on the limb.

FIGS. 6a and 6b illustrate a top view of a part of a tourniquet according to a fifth exemplifying embodiment, wherein FIG. 6a shows a state before a tension force is applied and FIG. 6b shows a state when a tension force is applied. In the fifth exemplifying embodiment, the tension sensor 8 is provided in an intermediate portion 5 of the tourniquet 1, the intermediate portion having a greater width than the width of the head portion 2 and the width of the loop portion 4, respectively. The intermediate portion further comprises an opening 9 through which the tail portion (not shown) can be passed. As shown in FIG. 6a, the tension sensor comprises two parallel cuts in the form of slits 20a that reach a first longitudinal edge 8a of the tension sensor as well as two parallel cuts in the form of slits 20b reaching to a second longitudinal edge 8b of the tension sensor 8. One of the slits 20a and one of the slits 20b are located in a first plane along the transverse axis of the strip. Correspondingly, the other one of the slits 20a and the other one of the slits 20b are located in a second plane that is also located in the transverse axis of the strip. The slits 20a and 20b may in other words be considered to be provided in two parallel rows, each row consisting of two slits. Midway between the rows, each comprising two slits, the tension sensor comprises a third cut in the form of a slit 20c that does not reach any one of the longitudinal edges 8a, 8b of the tension sensor. The third cut is parallel to the two rows of cuts. Furthermore, each of the slits 20a, 20b, 20c may, if desired, be provided with a small circular hole 26 at the ends of the slits. Such a hole 26 has the purpose of reducing the risk of the ends of the slits acting as break or tear initiation points due to sharpness of such ends.

As shown in FIG. 6b, when tension is applied to the tourniquet along the longitudinal axis of the tourniquet, the slits 20a, 20b and 20c will widen along the longitudinal axis. This will result in the slit 20c obtaining a shape similar to a sharp oval.

FIGS. 7a and 7b each illustrate a top view of a part of a tourniquet according to a sixth exemplifying embodiment, wherein FIG. 7a shows a state before tension has been applied and FIG. 7b shows a state wherein the tourniquet is subjected to a tension force. The sixth embodiment differs from the exemplifying embodiment shown in FIGS. 6a and 6b in that the tension sensor comprises a more numerous parallel rows of slits, each row comprising shorter, more numerous cuts (here slits). Every second row of slits comprises one slit which reaches to the first longitudinal edge 8a of the tension sensor, and another slit which reaches to the second longitudinal edge 8b of the tension sensor. In the FIGS. 7a and 7b, seven rows of slits are illustrated wherein four of the rows comprise slits that reach the longitudinal edges.

FIG. 8 illustrates a top view of a part of a tourniquet according to a seventh exemplifying embodiment before any tension has been applied to the tourniquet. The seventh exemplifying embodiment is similar to the exemplifying embodiment shown in FIGS. 6a and 6b. However, it differs in that the slits 20a, 20b reaching the longitudinal edges of the tension sensor are not perpendicular to the longitudinal axis of the tension sensor, but rather reaches the edges at an angle to the longitudinal axis as well as the transverse axis (where the transverse axis is the axis perpendicular to the longitudinal axis). Furthermore, instead of circular holes, the elongated holes 26' may be provided at the end of the respective slits.

In addition to the above described examples of different patterns of the cuts of the tension sensor, further possibilities exits. For example, FIG. 9 illustrates a top view of a part of a tourniquet according to an eight exemplifying embodiment wherein the tension sensor comprises a plurality of cuts 30, each cut having the shape of a plurality of semi-circles 30a adjoining each other along the longitudinal axis of the tension sensor (such as in the form of an extended figure "3"). Furthermore, the material present between two adjacent cuts forms a meandering path M of material. Two adjacent meandering paths M, M' are a mirror image of one another along the longitudinal axis of the tension sensor.

FIG. 10 illustrates yet another example in the form of a top view of a part of a tourniquet according to a ninth exemplifying embodiment. In this example, the tension sensor 8 comprises holes 32 having essentially the shape of a letter T, with a tapering pillar 33 of the T towards the base of the T and a roof of the T comprising thicker end portions 34 compared to the thickness of the roof where it meets the pillar 33. The T-cuts are arranged in two rows, one row featuring shorter T-cuts than the other. T-cuts within each row are separated from an adjacent T-cut by a longitudinal cut 35. Moreover, the rows of T-cuts are separated by additional cuts in the form of holes 36 of substantially triangular shape. The pattern of the cuts forms meandering paths, indicated by the dotted line M, between the cuts. The meandering paths in this exemplifying embodiment comprise parts $M_A$ which have a course that approximates the longitudinal axis of the tension sensor and the strip.

FIG. 11 illustrates a top view of a part of a tourniquet according to a tenth exemplifying embodiment, wherein the tension sensor comprises a pattern of cuts comprising a plurality of parallel rows, each row comprising more than one cut and wherein each cut is in the form of a slit 20. The rows are oriented along the transversal axis of the tourniquet, i.e. perpendicular to the longitudinal axis of the tension sensor. Every second row comprises a first slit 20a that reaches to the first longitudinal edge 8a of the tension sensor 8 and a second slit 20b that reaches to the second longitudinal edge 8b. The tension sensor further comprises a plurality of longitudinal cuts 20e. The longitudinal cuts 20e each intersect a slit 20 of a row that does not comprise any slits that reach the longitudinal edges of the tension sensor. Thus, the pattern of the cuts may be described as forming a plurality of rectangular meandering paths of material along the longitudinal axis of the tension sensor.

Irrespective of the exemplifying embodiment described herein, the tourniquet may comprise at least one indicator associated with the tension sensor. Examples of indicators include a pressure indicator element, an indicium or indicia. The purpose of indicator(s) is to visually illustrate to the user that the appropriate pressure has been achieved in the tourniquet. The indicium/indicia may for example constitute a print that changes shape or is only visible when the intended pressure by the tourniquet has been obtained. Alternatively, the indicator may constitute a ribbon or thread attached on a top surface or interwoven into the tension sensor, such that the ribbon or thread is meandering between the cuts of the tension sensor before the tourniquet has been subjected to a tension force and which obtains a straight shape when the intended pressure has been achieved. In the following, some additional examples will be illustrated.

Figure 12A:
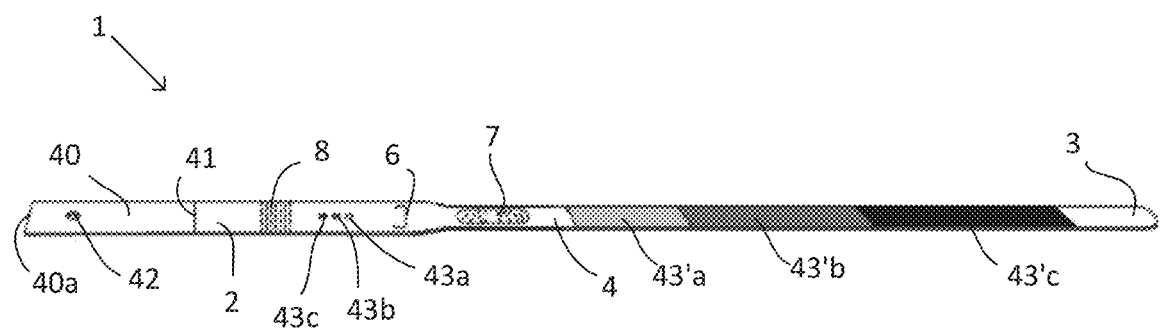
FIG. 12a illustrates a perspective view of a tourniquet according to an eleventh exemplifying embodiment before being subjected to tension.
Figure 12B:
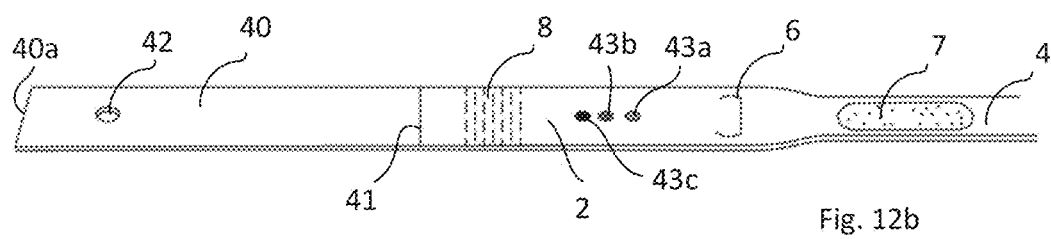
FIG. 12b illustrates a perspective view of a part of the tourniquet according to FIG. 12a before being subjected to tension, and prior to the head portion being folded
Figure 12C:
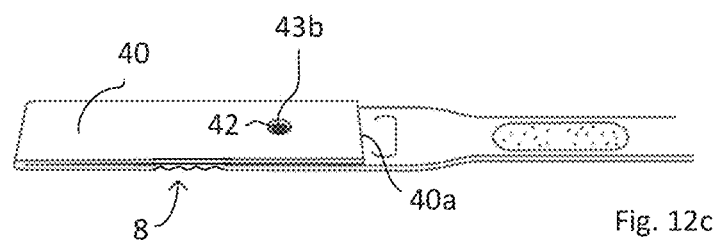
FIG. 12c illustrates a perspective view of a part of the tourniquet according to FIG. 12a during use and when subjected to tension.

FIG. 12a illustrates a perspective view of a tourniquet according to an eleventh exemplifying embodiment in the as produced condition before use. FIG. 12b illustrates a closer view of the tourniquet according to FIG. 12a in a part thereof. FIG. 12c illustrates a perspective view of a part of the tourniquet according to FIG. 12a during use when subjected to a predetermined tension force. This embodiment exemplifies compensation for difference in limb radii.

As shown in FIG. 12a, the tourniquet 1 comprises a pressure indicator element 40 attached to the longitudinal end of the head portion 2 by means of a fold 41 or the like. The pressure indicator element 40 further comprises a free end 40a. The pressure indicator element 40 is intended to be folded over the head portion 2 during use of the tourniquet, as shown in FIG. 12c, so that the tension sensor becomes located distally to the free end with respect to the longitudinal axis of the strip. In other words, the pressure indicator element spans the tension indicator when folded over the head portion 2. Furthermore, when the pressure indicator element 40 is folded over the head portion 2, the free end 40a of the pressure indicator element is movable over the surface of the strip along the longitudinal axis of the strip in response to the extension of the tension sensor 8.

The pressure indicator element 40 comprises an aperture 42 intended to cooperate with printed indicia, here illustrated as three dots 43a, 43b, 43c arranged in line along the longitudinal axis of the strip, on a top surface of the head portion 2 (or a possible intermediate portion). The dots 43a, 43b, 43c may for example have different colours so as to inform the user of the tension level applied. Other forms of indicia than coloured dots may however be plausible, for example patterns or geometrical shapes. Furthermore, each of indicia 43a, 43b, 43c is paired with corresponding indicia 43'a, 43b', 43'c on a top surface of the loop portion 4. For example, the dot 43a has the same colour as the indicium 43'a, the dot 43b has the same colour as the indicium 43'b etc. The indicia 43'a, 43'b, 43'c on the loop portion are related to the circumference of the limb to which the user applies the tourniquet.

During use, the tourniquet 1 is wrapped around a limb of interest and, depending on the circumference of said limb, one of the indicia 43'a, 43'b, 43'c of the loop portion will be threaded through the opening formed by the cut 6 when the tourniquet is pulled snug around the limb. This informs the user of which of the indicia 43a, 43b, 43c should be visible through the aperture 42 of the pressure indicator element 40 so that the intended appropriate pressure is onto the limb. As the tourniquet 1 is subjected to a tension force while the pressure indicator element 40 is folded over the head portion 2, the tension sensor 8 will be activated and extended. This in turn moves the pressure indicator element 40 with the aperture 42 in relation to the printed indicia 43a, 43b, 43c on the top surface of the head portion 2. When a first tension force has been achieved in the strip, the first dot 43a will become visible through the aperture 42. If the user continues to pull the strip, the tension force will increase such that the second dot 43b will become visible through the aperture 42. In FIG. 12c, the strip is illustrated in a state when subjected to an intended appropriate tension in case of a limb circumference corresponding to the indium 43'b since dot 43b is visible through the aperture 42 of the pressure indicator element 40. The number of tension levels can be more or fewer than three. More numerous tension levels, i.e. number of paired indicia in loop and pressure indicator element, generate increased pressure precision.

Figure 13A:
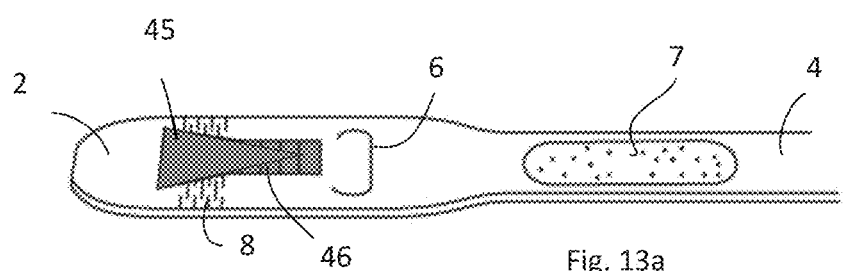
FIG. 13a illustrates a perspective view of a part of a tourniquet according to a twelfth exemplifying embodiment before being subjected to tension.
Figure 13B:
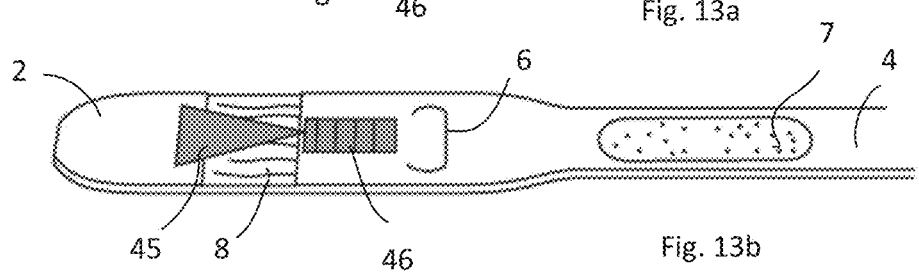
FIG. 13b illustrates a perspective view of the tourniquet according to FIG. 13a when subjected to tension.

FIGS. 13a and 13b illustrates a perspective view of a part of a tourniquet according to a twelfth exemplifying embodiment, wherein FIG. 13a illustrates the tourniquet before being subjected to a tension force and FIG. 13b illustrates the tourniquet when subjected to a tension force. In FIG. 13b, the extended tension sensor 8 is merely indicated by wavy lines for sake of demonstration. The tension sensor 8 is illustrated as being located in the head portion 2 of the strip. However, it is also possible to arrange the tension sensor in an intermediate portion. The strip comprises printed indicia, such as a printed pattern comprising a number of coloured boxes 46, on a top surface thereof on a first side of the tension sensor as seen along the longitudinal axis of the strip. The strip further comprises a pressure indicator element 45 attached to the upper side of the strip on a second side of the tension sensor as seen along the longitudinal axis of the strip. The pressure indicator element is adapted to function with the printed indicia. As illustrated in FIG. 13b, the pressure indicator element will move as a result of the extension caused by the tension force applied to activate the tension sensor. Thus, a part of the pressure indicator element will move in relation to the printed indicia, thereby informing the user of the tension force achieved in the tourniquet.

Figure 14A:
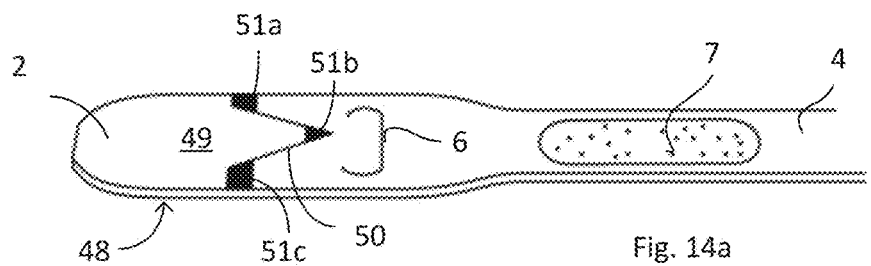
FIG. 14a illustrates a perspective view of a part of a tourniquet according to a thirteenth exemplifying embodiment before being subjected to tension.
Figure 14B:
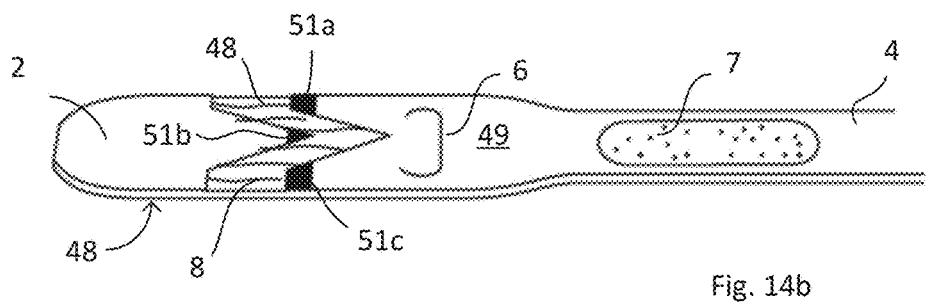
FIG. 14b illustrates a perspective view of the tourniquet according to FIG. 14a when subjected to tension.

FIGS. 14a and 14b illustrates a perspective view of a part of a tourniquet according to a thirteenth exemplifying embodiment, wherein FIG. 14a illustrates the tourniquet before being subjected to a tension force and FIG. 14b illustrates the tourniquet when subjected to a tension force. In this exemplifying embodiment, the strip comprises a first strip layer 48 and a second strip layer 49 superposed on the first strip layer 48. The second strip layer 49 reaches from the first longitudinal end of the strip to the second longitudinal end of the strip. Suitably, also the first strip layer reaches from the first longitudinal end of the strip to the second longitudinal end of the strip (as intended to be shown in FIGS. 14a and 14b), but this is not necessary.

The tension sensor 8 (partly visible in FIG. 14b in an activated state) is arranged in the first strip layer 48 and the second strip layer 49 comprises a perforation 50 that traverses from a first longitudinal edge of the second strip layer to a second longitudinal edge of the second strip layer. In the FIGS. 14a and 14b, the perforation is illustrated to traverse across the second strip layer in the form of a V with the tip of the V arranged midway between the longitudinal edges of the second strip layer. However, other forms are also plausible as long as the perforation 50 reaches across the longitudinal edges of the second strip layer. The perforation 50 is configured to rupture when the tourniquet 1 is subjected to a tension force along the longitudinal axis thereof and the tension sensor is activated. It should be noted that the perforation 50 may alternatively be replaced with a permanent cut in the second strip layer arranged in the same manner as the perforation 50. In other words, the second strip layer would be divided into two separate parts and achieve the same purpose without having to be ruptured when the strip is subjected to a tension force along the longitudinal axis.

The second strip layer 49 further comprises printed indicia associated with the tension sensor 8. In FIGS. 14a and 14b, this is illustrated in the form of three sub-lines 51a, 51b, 51c arranged along the transverse axis of the strip. As shown in FIG. 14b, the three sub-lines are provided such as to align into a single straight line when the appropriate tension has been achieved in the tourniquet, as determined by the intended extension of the tension sensor made possible by the patterned cuts (not specifically illustrated in FIGS. 14a and 14b). Before the tension sensor 8 has been activated, the central sub-line 51b of the three sub-lines is provided at the tip of the V and is parallel but offset with respect to the other two sub-lines 51a, 51c.

Figure 15A:
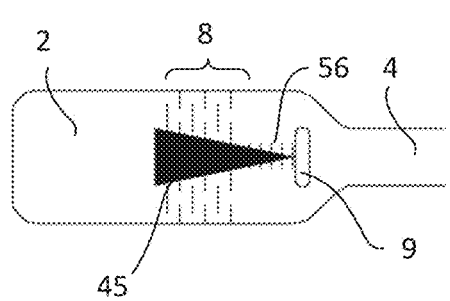
FIG. 15a illustrates a top view of a part of a tourniquet according to a fourteenth exemplifying embodiment before being subjected to tension.
Figure 15B:
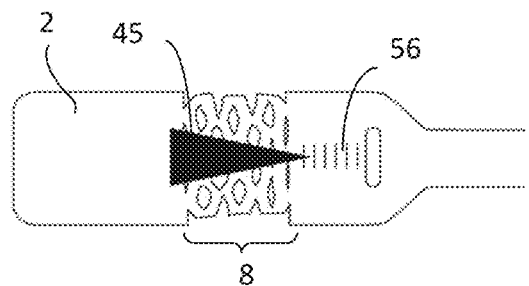
FIG. 15b illustrates a top view of the tourniquet according to FIG. 15a when subjected to tension.

FIGS. 15a and 15b illustrates a fourteenth exemplifying embodiment that corresponds to the exemplifying embodiment shown in FIGS. 13a and 13b, except that the printed coloured boxes 46 are replaced by a printed scale 56.

Figure 16A:
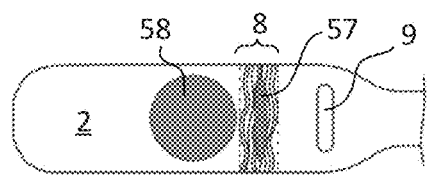
FIG. 16a illustrates a top view of a part of a tourniquet according to a fifteenth exemplifying embodiment before being subjected to tension.
Figure 16B:
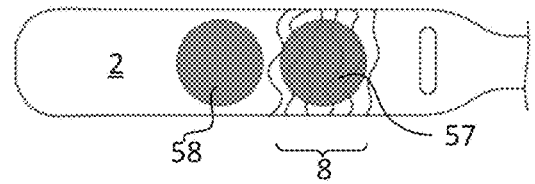
FIG. 16b illustrates a top view of the tourniquet according to FIG. 16a when subjected to tension.

FIGS. 16a and 16b illustrate a top view of a part of a tourniquet according to a fifteenth exemplifying embodiment, wherein FIG. 16a illustrate a state before the tourniquet is subjected to a tension force and FIG. 16b illustrates a state when the tourniquet is subjected to the intended appropriate tension force. In the figures, the tension sensor 8 is merely indicated by wavy lines for sake of demonstration. However, the tension sensor 8 comprises cuts provided in a predetermined pattern as previously described. The tension sensor may be planar in the plane of the strip as described in any of the preceding exemplifying embodiments. However, it is also plausible that the tension sensor is provided in the form of a corrugated shape, undulating about the plane of the strip, if desired. The tension sensor 8 comprises an indicium 57 on the top surface of the tension sensor. The indicium 57 is configured to obtain a predetermined shape only when the tension sensor has been activated and extended to the intended extension, corresponding to the intended tension force in the tourniquet. To facilitate for the user to determine that the indicium 57 has acquired the intended shape, a reference shape 58 may also be printed on the top surface of for example the head portion 2.

Figure 17A:
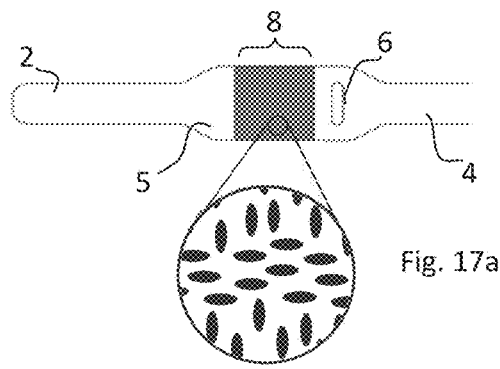
FIG. 17 illustrates a top view of a part of a tourniquet according to a sixteenth exemplifying embodiment, including a zoomed in portion.
Figure 17B:
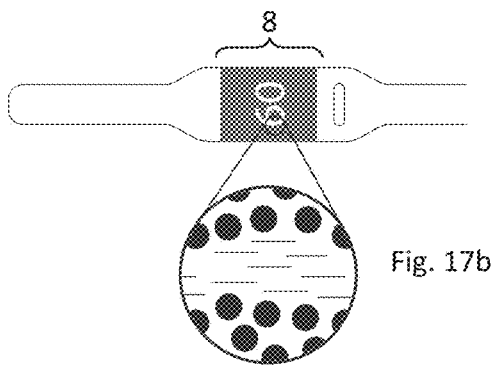

FIGS. 17a and 17b show a top view of a part of a tourniquet according to a sixteenth exemplifying embodiment, wherein the cuts in the tension sensor 8 comprises microscopic cuts as illustrated by the zoomed in portion. FIGS. 17a and 17b show the part of the tourniquet before being subjected to a tension force and while being subjected to a tension force, respectively. In the present context, microscopic cuts shall be considered to mean cuts which have a size, in the longest extension thereof, of less than 1 mm. Upon being subjected to sufficient tension, cuts change shape and/or orientation, revealing macroscopic tourniquet indicia as exemplified in FIG. 16b. Such macroscopic indicia may suitably comprise indicia that indicate the achieved pressure level (here exemplified in units of mmHg), geometric indicia such as indicia 57 shown in FIGS. 16a and 16b, or reveal other types of indicia upon being subjected to tension.

In the example micropattern shown in FIGS. 17a and 17b, non-circular cuts in the shape of ellipses oriented along the longitudinal or transverse axis of the tourniquet prior to tension (see FIG. 17a) take on linear or circular geometry, respectively, upon being subjected to tension (see FIG. 17b). The visual contrast between linear and circular geometry cuts is greater than that of perpendicularly oriented ellipses, so a pre-determined plurality of cuts may be ordered to reveal indicia when subjected to tension.

In addition to this pattern of cuts, cuts may for example revolve and/or move within the pattern, plausibly when combined with larger cuts along the longitudinal axis of the tension sensor (see FIGS. 4a and 4b). Combinations of such patterns make it possible to reveal one or several complex indicia upon application of different amounts of tension.

FIGS. 18a and 18b illustrate a top view of a part of a tourniquet according to a seventeenth exemplifying embodiment, before being subjected to a tension force and while being subjected to a tension force, respectively. The seventeenth exemplifying embodiment is similar to the exemplifying embodiment shown in FIGS. 7a and 7b with a difference in that the strip does not comprise any intermediate portion. The tension sensor 8 and the opening 9 are instead provided in the head portion 2 of the strip. Furthermore, the strip comprises a pressure indicator element 60 arranged in the same plane as the rest of the strip. The pressure indicator element 60 is connected to a longitudinal edge 2a of the head portion and comprises a free end 60a. The pressure indicator element 60 is in the same plane as the head portion and bridges the tension sensor 8, and is intended to be read together with for example a scale printed on a top surface of the head portion, as shown in the FIGS. 18a and 18b. In other words, the position of the free end 60a of the pressure indicator element 60 is read in relation to the scale 61. This exemplifying embodiment, as well as the exemplifying embodiment shown in FIGS. 15a and 15b have the advantage of enabling the reading of different pressure levels, and may therefore be suitable in applications where differential pressure may be desired depending on the situation.

FIGS. 18a and 18b illustrate the tension sensor 8 as having the same width as the width of the head portion. As an alternative, the width of the tension sensor 8 may be decreased to allow the pressure indicator element 60 to be fitted alongside the tension sensor without locally increasing the width of the head portion 2. Constant width of the head portion may in some cases facilitate production of the tourniquet.

FIGS. 19a and 19b illustrate a top view of a part of a tourniquet according to an eighteenth exemplifying embodiment which is similar to the exemplifying embodiment shown in FIGS. 18a and 18b. However, instead of the pressure indicator element 60, the tourniquet shown in FIGS. 19a and 19b comprises a pressure indicator element tab 62 that is connected to a longitudinal edge 2a of the head portion 2 by means of a fold 63. The pressure indicator element tab 62 further comprises a free end 62a. When the tourniquet is to be used, the pressure indicator element tab 62 is folded over the head portion 2 so as to cover the tension sensor 8, as shown in FIG. 19b. Thus, the free end 62a is arranged on a longitudinally opposite side of the tension sensor as to the fold 63 where the pressure indicator element tab 62 is connected to the head portion. If desired, the head portion may also comprise an adhesive 66 on a top surface thereof, the purpose of such an adhesive is to ensure that the pressure indicator element tab is arranged firmly in place when the pressure indicator element tab has been folded over the head portion.

The pressure indicator element tab 62 comprises for example two apertures 64a, 64b in the vicinity of the free end 62a. Furthermore, the head portion comprises at least one an indicium 65 printed on the top surface thereof. When the tension sensor is activated, the free end 62a of the pressure indicator element tab 62 will move distally together with the head portion along the longitudinal axis as a result of the extension of the tension sensor 8. Thereby, the apertures 64a, 64b will move in relation to the indicium 65, and when the indicium 65 is visible through one of the apertures, the user will be able to easily see that the intended tension force has been achieved.

A combination of different indicators, including indicia and/or pressure indicator elements, explained above with respect to different exemplifying embodiments, may be used to ensure fail-safe pressure reading. Thus, the present invention is not limited by the specific indicators described above.

FIG. 20 illustrates a top view of a tourniquet 1 according to a nineteenth exemplifying embodiment. For sake of clarity, the tension sensor 8 has been omitted in the figure. The tension sensor may however be in accordance with any one of the previously disclosed exemplifying embodiments. The tourniquet according to the nineteenth embodiment comprises a loop portion with varying width along the longitudinal axis of the strip, more specifically tapering from the head portion 2 towards the tail portion 3. Furthermore, the tail portion 3 has a width that is greater than the width of the loop portion at the longitudinal end thereof where it connects to the tail portion 3. The tail portion 3 however has a smaller width than the width of the head portion. This configuration of the strip of the tourniquet has the advantage of enabling the tourniquet to be used on both a limb having a small circumference (for example an arm of a child) and a limb having a large circumference (for example an arm of an adult muscular person) and while still enabling a suitable pressure in either case. A limb with a smaller circumference would in this case be subjected to a larger width in the loop portion, and a limb with larger circumference is subject to the desired pressure due to the smaller width of the loop portion in the vicinity of the tail portion. This embodiment may achieve either a correct average pressure about the limb, regardless of circumference, or the sought pressure near or at the hole 6 where the tail is threaded through the head; the point at which limb circumference is defined. The fact that the tail portion has a greater width than the adjacent loop portion may for example facilitate gripping of the tail portion when applying the tension force along the longitudinal axis of the strip.

FIG. 21 illustrates a top view of a tourniquet according to a twentieth exemplifying embodiment similar to the exemplifying embodiment shown in FIG. 20 but wherein the width of the tail portion also tapers, like the loop portion, towards the second longitudinal end of the strip. In FIG. 21, the tension sensor has been omitted for sake of clarity. However, the tourniquet may comprise a tension sensor in accordance with any one of the previously disclosed exemplifying embodiments. The configuration of the strip shown in FIG. 21 has the same advantage of taking into account different circumferences of limbs as disclosed above with reference to FIG. 20.

Figure 22A:
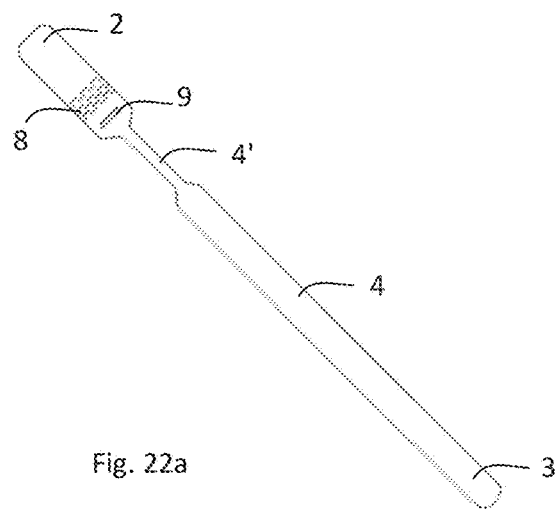
FIG. 22a illustrates a top view of a tourniquet according to a twenty-first exemplifying embodiment before being subjected to tension.
Figure 22B:
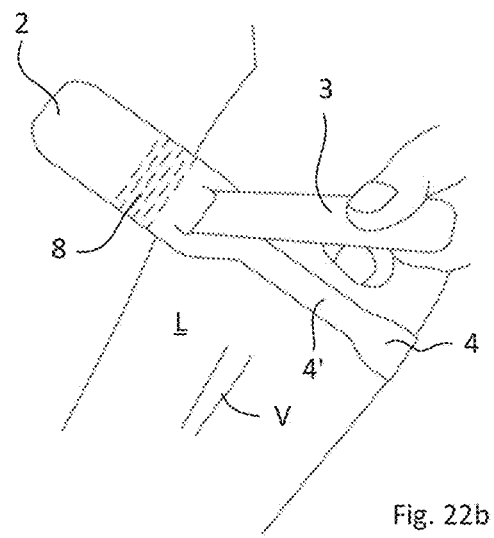
FIG. 22b illustrates a perspective view of the tourniquet according to FIG. 22a, when applied around a limb, before being subjected to tension.

FIGS. 22a and 22b illustrate a top view and a perspective view, respectively, of a tourniquet according to a twenty-first exemplifying embodiment. The tourniquet is similar to the tourniquet described in relation to the exemplifying embodiment shown in FIGS. 7a and 7b. However, the loop portion 4 also comprises a region 4' with a reduced width compared to the rest of the loop region 4. Said region 4' is arranged in the vicinity of the opening 9 adapted for passing the tail portion 3 through when the loop region has been wrapped around a limb L. This is illustrated in FIG. 22b where the user has just passed the tail region through the opening but has not yet started pulling both longitudinal ends of the strip.

The purpose of the region 4' having differential width compared to the rest of the loop portion is to locally obtain a different pressure. In this example, the loop portion 4' is located at the part of the limb L where the vein V that is intended to be punctured is located. The smaller width of region 4' causes a higher local pressure over the vein V, while the higher width in the rest of the loop portion 4 keeps the rest of the limb subjected to lower pressure upon the same amount of tensile force used. This may result in increased comfort for the patient.

Figure 23A:
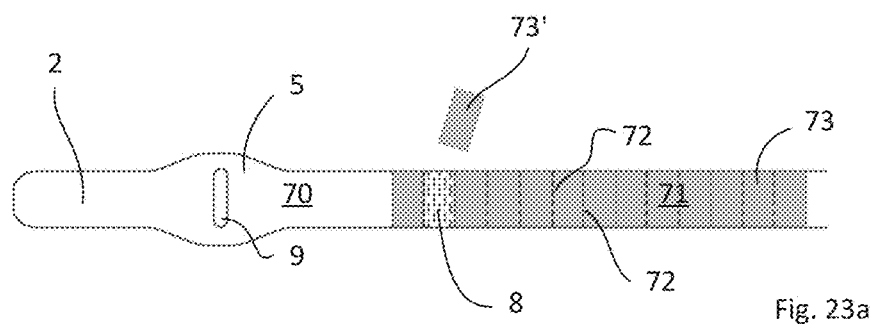
FIG. 23a illustrates a top view of a part of a tourniquet according to a twenty-second exemplifying embodiment before being subjected to tension.
Figure 23B:
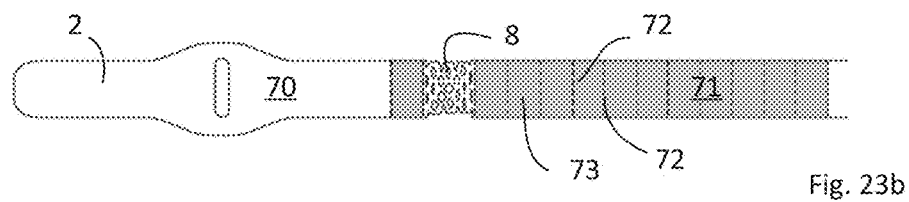
FIG. 23b illustrates a top view of the tourniquet according to FIG. 23a when subjected to tension.

It may be desirable to have a tourniquet which is capable of being used for limbs of very varying sizes, i.e. limbs that have very different circumferences. FIGS. 23a and 23b illustrate an exemplifying embodiment of the tourniquet according to the present invention, which may take this into account. FIG. 23a illustrates a top view of a part of such a tourniquet before being subjected to a tension force, and FIG. 23b illustrates a top view of a part of such a tourniquet when subjected to a tension force such that a tension sensor 8 is activated. The tourniquet comprises a strip having a first strip layer 70 and a second strip layer 71, the second strip layer being superposed on the first strip layer and attached thereto by means of for example an adhesive, local fusion or other means.

The second strip layer 71 may be present only on the loop portion 4, or on the whole strip from the first longitudinal end to the second longitudinal end. In FIGS. 23a and 23b, the second strip layer is shown as only present in the loop portion in order to enable also showing the first strip layer 70. The first strip layer 70 extends from one longitudinal end of the strip to the second longitudinal end of the strip. The second strip layer 71 is made of a substantially inelastic material and will therefore not be elongated along the longitudinal axis when the tourniquet is subjected to tension.

The second layer 71 comprises a plurality of transverse perforations 72 arranged in parallel to each other, each perforation traversing the full tourniquet width between the longitudinal edges of the loop portion. These perforations may also be accompanied by local, adjacent sites of bonding to the underlying first strip layer 70, for example by local fusion of layers 70 and 71. The purpose of the perforations is to enable the user to remove a portion 73 of the second layer when the tourniquet is to be used, as shown in FIG. 23a by an already removed portion 73' of the second strip layer 71.

The first layer 70 comprises a number of tension sensors 8 arranged in line along the longitudinal axis of the loop portion 4. Each tension sensor 8 is located immediately below a portion 73 of the second layer 71 which may be removed. Thus, upon removal of a portion 73 of the second strip layer 71 between two adjacent perforations 72, the tension sensor 8 arranged in the first strip layer 70 below the removed portion is exposed and rendered operable. By selecting different portions 73 of the second strip layer, the user can select where the operable tension sensor will be arranged along the longitudinal axis of the loop region 4. The amount of sensor extension as a function of tensile force may vary along the longitudinal length of the loop region. In other words, the tourniquet may be described as comprising a plurality of tension sensors, wherein at least a first tension sensor has a Young's modulus different than a Young's modulus of a second tension sensor of the plurality of tension sensors; and wherein the Young's modulus of an individual tension sensor of the plurality of tension sensors is a function of the location of the individual tension sensor along the longitudinal axis of the strip.

During use of the tourniquet 1 as shown in FIGS. 23a and 23b, the sensor that is rendered operable is chosen based on limb circumference, so that limb circumference is compensated for in the Young's modulus of the sensor. The remaining tension sensors will be covered by the second strip layer 71 and thus remain inactive when the tourniquet is subjected to the tension force. In addition, indicia may be revealed once a sensor is rendered operable.

Figure 24A:
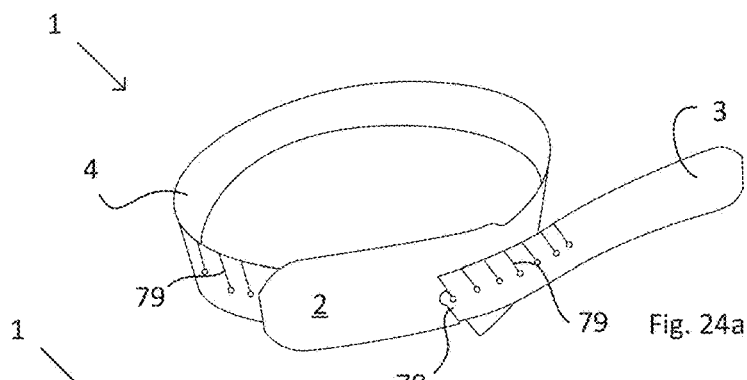
FIG. 24a illustrates a perspective view of a tourniquet according to a twenty-third exemplifying embodiment.
Figure 24B:
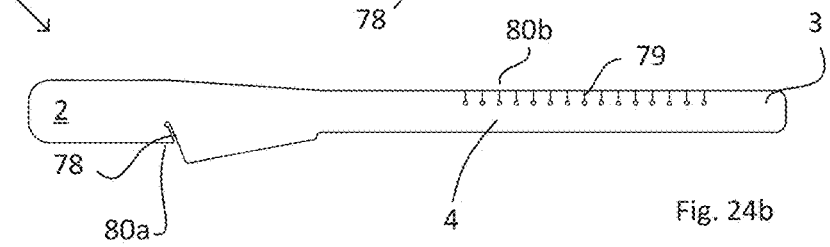

Irrespective of the exemplifying embodiment of the tourniquet as described herein, it is preferred that the tourniquet comprises an enclosed opening, in general illustrated with the reference number 9 herein, which is configured to allow the tail portion to pass through such that the tail portion may be overlapping the loop portion. Such an enclosed opening ensures that the tension force is applied along the intended tourniquet axis and therefore reduces the risk of shear stress. The present invention is however not limited thereto. The tourniquet may have other configurations ensuring that the tail portion can substantially overlap the loop portion when the loop portion has been wrapped around a limb. FIGS. 24a and 24b illustrate such an example.

FIG. 24a illustrates a perspective view of a tourniquet according to a twenty-third exemplifying embodiment and FIG. 24b illustrates a top view of the tourniquet shown in FIG. 24a. The tension sensor has been omitted in the figures in order to more clearly demonstrate the features intended to be specifically shown. The tourniquet 1 may comprise any one of the tension sensors described above with reference to the previously discussed exemplifying embodiments. The tourniquet 1 comprises a first recess 78 at a first longitudinal edge 80a of the strip in the head portion 2. The tourniquet may further comprise a plurality of second recess 79 in a second longitudinal edge 80b of the strip, the second recesses 79 arranged in parallel and in the loop portion 4. The first recess 78 is adapted to be mated with one of the second recesses 79 corresponding to a length of the loop portion 4 when the intended tension force has been achieved in the tourniquet 1 wrapped around a limb. The tail portion 3, or the head portion 2, may thereafter be fastened to the loop portion 4 in any conventional manner, such as by means of an adhesive (not shown). By placing the fastening mechanism so that fastening requires the longitudinal central axis of each tourniquet end to coincide, shear stress in the sensor pattern is minimised.

The material of the strip used for producing the tourniquet according to the present invention is preferably a substantially inelastic material as previously disclosed. Such a material retains essentially the same width of the tourniquet when subjected to a tension force, and therefore provides consistent pressure to the limb during use. Pressure corresponds to force per unit area in contact with the limb, and therefore it is desirable to have a tourniquet that retains a constant width (at least in the loop region) when subjected to a tensile force to tighten the tourniquet around the limb in order to reliably apply certain pressure to the limb.

The present invention may however also be used in a strip made of an elastic material as used in previously known tourniquets, for example a strip made of rubber or silicone. Such a material usually has a positive Poisson ratio and therefore achieves a reduced width when subjected to a tension force along the longitudinal axis of the strip. A non-intended or difficult to control reduction in width of the tourniquet in the loop portion thereof when pulled alters the pressure applied by the tourniquet. In order to counter-act such uncontrolled reduction in width, the loop portion should preferably contain cuts arranged in an auxetic pattern. Thereby, reduction in width of the loop portion will be reduced or compensated for since auxetic pattern cuts widen the loop portion in the direction perpendicular to the applied tension. Thereby, a width can either be maintained constant, enabling for precision pressure, or reduced in a controlled manner, which can compensate for differential limb circumference when using a certain tension force. FIGS. 25a and 25b illustrates a top view of a part of the loop portion of a tourniquet made of an elastic material according to a twenty-fourth exemplifying embodiment, before being subjected to a tension force and when subjected to a tension force, respectively. The loop portion 4 comprises a plurality of cuts 83 constituting holes and provided in an example auxetic pattern. This auxetic pattern region may constitute part of the tension sensor. Alternatively, the cuts 83 provided in an auxetic pattern does not form a part of the tension sensor.

The tourniquet according to the present invention may suitably be produced by manufacturing a band material and cutting the band material so as to achieve the different portions of the strip and the cuts, slits, holes, openings and apertures therein as disclosed above. The tourniquet may be produced to a single tourniquet. However, it is also plausible to manufacture an elongated band comprising a plurality of tourniquets connected to each other, one longitudinal end to another longitudinal end, the band provided with a perforation between two adjacent tourniquets such that each tourniquet can easily be separated/detached from an adjacent tourniquet by tearing or the like by a user intending to collect a single tourniquet. The elongated band may suitably be provided in a housing comprising an opening through which the band may exit so as to enable collection of a single tourniquet by a user when desired. This housing may be sterile. The elongated band may for example be provided in a roll inside the housing or be arranged in a zigzag way such that the tourniquets of the elongated band are substantially flat inside the housing and arranged one on another. The housing and the elongated band together form a tourniquet dispenser.

FIG. 26 illustrates an example of such a dispenser 85 comprising a housing 86 having an opening 87 for retrieving a tourniquet from the elongated band present inside the housing, which may be sterile. The packaging opening may be of firm material, possibly functionalised by metal.

The force used to retrieve a band could shape the band ahead of usage. It is possible to create a crease line in the tourniquet during production and, in the process of pulling down and tearing off the tourniquet at the exit of the tourniquet from the packaging, the fold is actuated in its 3D-form, allowing extra 3D functionality.

Packaging may come with double-sided tape on the bottom, accessible by peeling off a sticker backer, so to allow securing the packaging to a surface. This would facilitate single-handed band retrieval. Decreased contact with the packaging also decreases spread of bacteria in the clinical setting.

Moreover, the tourniquet according to the present invention may be sold to a customer in the form of a kit comprising the tourniquet and at least one additional component intended for use together with the tourniquet. FIG. 27 illustrates a top view of an example of such a kit 88. The kit 88 comprises a tourniquet 1 as described above, a syringe 89 and a swab 90 intended for sterilising a part of the skin of the limb before puncture by means of the needle of the syringe 89. In addition to the tourniquet 1, the kit may suitably contain other components instead of, or in addition to, the syringe 89 and the swab 90. Such components may be a pair of gloves, a tray, flush syringe, dressing, gauze sponges, specimen bag, adhesive bandage, tape, at least one blood collection tube, bottle of alcohol, one or more swab sticks, pen, alcohol pad, surgical or face mask, IV tubing extension set, some form of medicament such as an analgesic, and paper cloth. The kit further comprises an outer packaging 91 enclosing the components present therein, where such packaging may be sterile.

FIG. 28 illustrates a top view of a part of a tourniquet according to a twenty-fifth exemplifying embodiment. The figure illustrates a tension sensor arranged in the head portion 2, however the tension sensor may be arranged in any portion of the tourniquet as described above. Furthermore, even though the tension sensor is shown as comprising a plurality of cuts in the form of slits, any other configuration and pattern of the cuts of the tension sensor as disclosed above may be used. As shown in FIG. 28, the strip further comprises a limitation member 95 on each side of the tension sensor 8 and in the same plane as the tension sensor 8. Each limitation member is connected to a longitudinal edge of the strip on either side of the tension sensor and is shaped in a curved configuration in the plane coinciding with the longitudinal axis of the strip. The purpose of the limitation members 95 is to ensure that the tension sensor cannot be extended to an undesirable extension, such as a pressure causing discomfort to the patient. Therefore, the limitation members are intended to be straightened out when the tension sensor is activated but avoid further extension of the tension sensor than intended. It should however be noted that during normal use of the tourniquet as intended, the limitation members 95 are not intended to be fully straightened out. They serve as an additional protection against applying an excessive pressure onto the limb. There may be more than two limitation members. Limitation members may also serve as elements that give the tension sensor more elasticity. For example, the limitation members may assist in retraction of the extended tension sensor, which could stop the sensor from tearing.

FIG. 29 illustrates a top view of a tourniquet according to a twenty-sixth exemplifying embodiment. The tourniquet 1 shown in FIG. 29 comprises a tension sensor 8 in an intermediate portion 5. The tension sensor is arranged between the head portion and the cut 6 which forms an opening adapted for passing through the tail portion 3 when the loop portion 4 has been wrapped around a limb such as to encircle the limb. It should however be noted that the tension sensor need not be arranged as shown in FIG. 29, but can be arranged anywhere along the longitudinal axis of the strip as disclosed above. Furthermore, the tension sensor may comprise cuts in a predetermined pattern as disclosed above, and is not limited to the pattern shown in FIG. 29. The tourniquet 1 shown in FIG. 29 further comprises a print P on a top surface in the loop portion 4. The purpose of the print P is to inform a user of the relevant area of the loop region that may be used. In other words, the tourniquet comprises indicia adapted to inform the user when the limb circumference is within an acceptable range necessary for applying the appropriate intended pressure. This solution thus limits the error in pressure amount exerted by limiting tourniquet use to certain limb circumferences only. The indicium in the form of the print P is here illustrated as an interval indicated by a double-sided arrow. However, there may be other alternatives, for example as shown in FIG. 12a.

The tourniquet according to the present invention is not limited to the embodiments shown in the figures and discussed above, but may be varied within the scope of the appended claims.

For example, when the tourniquet comprises an adhesive for locking the tourniquet with the intended tension, the adhesive may be arranged on the loop region as shown for example in FIG. 1, or alternatively, the adhesive may be arranged on the tail portion to lock against the loop portion as shown in FIGS. 5a to 5c. The adhesive may alternatively be arranged on the head portion for locking against the loop portion. The adhesive may in certain instances also be arranged on the tension sensor as such. The adhesive may suitably be covered by a protective, peelable liner.

The fastening mechanism (such as the adhesive) may suitably be placed closer to a longitudinal end of the strip than the tension sensor such that the tension sensor extension is retained post-attachment, thereby showing the sensor value. The present invention is however not limited thereto as it in many cases may be sufficient to know the applied pressure only when fastening the overlapping portions of the tourniquet to retain compression.

Furthermore, the tourniquet may comprise other types of means for fastening and retaining the intended tension. For example, the adhesive may be replaced by hooks and loops (also known as Velcro®), which may be arranged in any of the locations described above with reference to the adhesive. It may even be plausible to use a buckle or clamp if desired, even though this is less preferred.

The tension sensor may comprise one single meandering path of strip material between the cuts, the meandering path extending from one longitudinal end of the tension sensor to the opposite longitudinal end of the tension sensor. In most cases, the tension sensor however comprises a plurality of meandering paths. These meandering paths may have the same length or have different lengths. For example, a first subset of meandering paths may have a first length and a second subset of meandering paths may have a second length different than the first length. Furthermore, the meandering paths may be parallel or non-parallel to each other. Two adjacent meandering paths may be a mirror image of one another along an axis parallel to or coinciding with the longitudinal central axis of the tension sensor. Moreover, the meandering paths may have the same or different geometrical configurations as each other. All of the above given possibilities are a result of how the cuts in the tension sensor are arranged.

The tourniquet may also be provided with means for increasing the comfort of the tourniquet during use thereof on a patient. This may for example be implemented by addition of a surface coating for reducing the friction between the tourniquet and the skin of a patient. Furthermore, the edges of the tourniquet may if desired be rounded, perforated or subject to alternative geometric configuration, or otherwise be subjected to a softening process such as to avoid the edges of the tourniquet damaging or cutting into the skin of the patient during use. In instances where the longitudinal edge bends away from the patient limb upon application of tension, the effective loop width decreases, allowing a higher local pressure. This has the added advantage that the wider width of the tourniquet—while not used to impose pressure—may be used for print, allowing for example printed instructions.

Furthermore, the head portion and/or the tail portion may be provided with an anti-slip coating, perforation or protrusions to increase local friction, thereby ensuring a better grip to these portions during use of the tourniquet.

While certain sensor patterns have been described in detail with particular reference to the disclosed embodiments, it will be understood that variations and modifications can be affected within the scope of the present invention. Further, sensor pattern behaviour is a function of choice of pattern, its associated geometric pattern variables, choice of material and possible reinforcement thereof, as exemplified by limitation members.

The tourniquet according to the present invention can take into account different circumferences of limbs. Sensor target pressure, pressure precision, tourniquet length and tourniquet width may be varied to accommodate different limbs, subpopulations of patients and tourniquet user preference. Examples of subpopulations where lower pressure may be applicable includes children and elderly patients, but could also include certain species of animal treated in veterinary sciences. Preferably, the loop portion may be configured for taking into account different limb circumferences while still applying an intended pressure to the limb corresponding to a tension force as determined by the tension sensor (compare for example with FIGS. 12a-12c, FIG. 20, FIG. 21 as well as FIGS. 23a and 23b).

Furthermore, it will be readily understood by the skilled person that the tourniquet according to the present invention may be adapted for use for a specific limb circumference, or more accurately a specific range of limb circumferences, only without departing from the scope of the present invention (compare for example with FIG. 29).

The invention claimed is:

1. A tourniquet comprising a strip having a longitudinal axis, a head portion at a first longitudinal end of the strip, a tail portion at a second longitudinal end of the strip, and a loop portion between the head portion and the tail portion, the loop portion having a sufficient length to encircle a limb of a human or animal, wherein the strip further comprises a tension sensor having a first longitudinal end and a second longitudinal end, the tension sensor comprising a plurality of cuts arranged in a predetermined pattern, wherein the pattern forms at least one meandering path of material defined between individual cuts of the plurality of cuts, the meandering path extending from the first longitudinal end of the tension sensor to the second longitudinal end of the tension sensor, the plurality of cuts hindering a linear shortest available path, through the material of the strip, that links the first longitudinal end of the tension sensor and the second longitudinal end of the tension sensor.

2. The tourniquet according to claim 1, wherein the tension sensor comprises a first longitudinal edge and a second longitudinal edge, wherein a first cut of the plurality of cuts reaches to the first longitudinal edge, and a second cut of the plurality of cuts reaches to the second longitudinal edge.

3. The tourniquet according to claim 1, wherein strip comprises an indicium adapted to inform a user when a circumference of the limb is within an acceptable range necessary for applying an intended appropriate pressure to the limb corresponding to a tension force as determined by the tension sensor.

4. The tourniquet according to claim 1, wherein the loop portion is configured for taking into account different limb circumferences in order to apply an intended pressure to the limb that is correlated to the applied tension force as determined by the tension sensor.

5. The tourniquet according to claim 1, wherein the strip is made of substantially inelastic material.

6. The tourniquet according to claim 1, wherein the strip further comprises an intermediate portion arranged between the head portion and the loop portion, the intermediate portion having a greater width than a width of the loop portion.

7. The tourniquet according to claim 6, wherein the tension sensor is arranged in the intermediate portion.

8. The tourniquet according to claim 7, wherein the cuts are in the form of holes, the loop portion has the same width as the head portion, and wherein the tension sensor is adapted to obtain the same width as the head portion and the loop portion when an intended tension force is applied.

9. The tourniquet according claim 1, the strip further comprising an opening configured for allowing the tail portion, and optionally at least a portion of the loop portion, to pass through the opening.

10. The tourniquet according to claim 1, wherein the plurality of cuts comprises a plurality of slits.

11. The tourniquet according to claim 10, wherein some of the slits are oriented perpendicular to the longitudinal axis of the strip, or wherein all of the slits are oriented perpendicular to the longitudinal axis of the strip.

12. The tourniquet according to claim 11, wherein the slits that are oriented perpendicular to the longitudinal axis of the strip are arranged in a plurality of parallel rows, each row comprising more than one slit.

13. The tourniquet according to claim 1, wherein the strip comprises a first strip layer and a second strip layer superimposed on the first strip layer, wherein the tension sensor is arranged in the first strip layer.

14. The tourniquet according to claim 13, wherein the second strip layer is divided along the transverse axis of the strip into two separate parts.

15. The tourniquet according to claim 13, wherein the second strip layer comprises at least one perforation traversing from a first longitudinal edge of the second strip layer to a second longitudinal edge of the second strip layer.

16. The tourniquet according to claim 15, wherein the perforation is configured to rupture when the tourniquet is subjected to a tension force applied by a user pulling the tourniquet along the longitudinal axis such that the second strip layer will be divided into two separate parts.

17. The tourniquet according to claim 15, wherein the second strip layer comprises a plurality of parallel perforations each traversing from a first longitudinal edge to a second longitudinal edge, the second strip layer comprising a number of removable portions each defined by two adjacent parallel perforations, and wherein the first strip layer comprises a plurality of tension sensors arranged along the longitudinal axis of the loop portion, each tension sensor comprising a plurality of cuts arranged in a predetermined pattern, wherein the pattern forms at least one meandering path of material defined between individual cuts of the plurality of cuts, the meandering path extending from the first longitudinal end of the tension sensor to the second longitudinal end of the tension sensor, and wherein each tension sensor is arranged below one of the removable portions of the second strip layer such that when one removable portion of the second strip layer is removed, the tension sensor arranged below the removed portion is rendered operable.

18. The tourniquet according to claim 17, wherein at least a first tension sensor of the plurality of tension sensors has a different Young's modulus compared to a second tension sensor of the plurality of tension sensors, and wherein the Young's modulus of an individual tension sensor is a function of the location of the individual tension sensor along the longitudinal axis of the strip in the loop portion.

19. The tourniquet according to claim 1, wherein the loop portion has a width that tapers towards the tail portion.

20. The tourniquet according to claim 1, further comprising a pressure indicator element attached to the strip at a first side of the tension sensor as seen along the longitudinal axis of the strip, the pressure indicator element extending past the tension sensor as seen along the longitudinal axis of the strip such that a free end of the pressure indicator element is arranged on a second side of the tension sensor as seen along the longitudinal axis of the strip.

21. The tourniquet according to claim 20, wherein the pressure indicator element is foldable about the strip such that, during use of the tourniquet, it is adapted to be arranged above or under the tension sensor.

22. The tourniquet according to claim 20, wherein the pressure indicator element comprises an aperture configured to function with an indicium or indicia present on a surface of the strip to thereby visually inform a user when an intended appropriate pressure has been achieved.

23. The tourniquet according to claim 1, wherein the strip is made of an elastic material, and the loop portion contains a plurality of cuts that are provided in an auxetic pattern.

24. The tourniquet according to claim 1, further comprising at least one indicium associated with the tension sensor and adapted to visually illustrate when the intended pressure is exerted by the tourniquet.

25. The tourniquet according to claim 1, further comprising at least one limitation member that is connected to a point on the first longitudinal edge of the strip, where this point is adjacent to the tension sensor, and also connected to a second point along the first longitudinal edge of the strip, were this second point is adjacent to the tension sensor and in a different location to the first point, the limitation member being configured to be straightened in response to the extension of the tension sensor when the tourniquet is subjected to a tension force, the limitation member preferably provided in the same plane as the strip.

26. The tourniquet according to claim 1, further comprising means for fastening overlapping portions of the strip when the loop portion is encircling a limb while applying a pressure to the limb.

27. An elongated continuous tourniquet band comprising a plurality of tourniquets according to claim 1, said tourniquets being detachably connected to one another, longitudinal end to longitudinal end.

28. A dispenser comprising a housing, an elongated continuous tourniquet band according to claim 27 rolled into a roll or arranged in a zigzag arrangement and packaged in said housing, the housing comprising an opening from which the elongated continuous tourniquet band can be drawn out to reveal a tourniquet one at a time for separation from the remainder of the elongated continuous tourniquet band, preferably wherein the housing is a sterile housing.

29. A kit comprising a package, a tourniquet according to claim 1, and at least one additional component provided in the package, the additional component preferably selected from the group consisting of a syringe, a pair of gloves, a tray, a swab adapted for disinfection, one or more absorption swabs, flush syringe, dressing, gauze sponges, specimen bag, adhesive bandage, tape, one or more blood collection tubes, bottle of alcohol, one or more swab sticks, pen, one or more antiseptic wipes such as alcohol pads, surgical or face mask, IV tubing extension set, some form of medicament such as an analgesic, and paper cloth.

* * * * *